US006818234B1

(12) United States Patent
Nair et al.

(10) Patent No.: US 6,818,234 B1
(45) Date of Patent: Nov. 16, 2004

(54) DIETARY FOOD SUPPLEMENT CONTAINING NATURAL CYCLOOXYGENASE INHIBITORS AND METHODS FOR INHIBITING PAIN AND INFLAMMATION

(75) Inventors: Muraleedharan G. Nair, Okemos, MI (US); Haibo Wang, Fresno, CA (US); David L. Dewitt, Okemos, MI (US); David W. Krempin, Temecula, CA (US); Dipak K. Mody, Temecula, CA (US); Yong Qian, San Diego, CA (US); David G. Groh, Temecula, CA (US); Audra J. Davies, Long Beach, CA (US); Mary A. Murray, Irvine, CA (US); Robin Dykhouse, Newport Beach, CA (US); Marc Lemay, Long Beach, CA (US)

(73) Assignees: Access Business Group International LLC, Ada, MI (US); Michigan State University, East Lansing, MI (US)

( * ) Notice: Subject to any disclaimer, the term of this patent is extended or adjusted under 35 U.S.C. 154(b) by 0 days.

(21) Appl. No.: 10/084,575

(22) Filed: Feb. 27, 2002

Related U.S. Application Data

(63) Continuation-in-part of application No. PCT/US00/23423, filed on Aug. 25, 2000.
(60) Provisional application No. 60/151,280, filed on Aug. 27, 1999, and provisional application No. 60/151,278, filed on Aug. 27, 1999.

(51) Int. Cl.$^7$ .............................................. A61K 35/78
(52) U.S. Cl. ....................... 424/777; 424/732; 424/725; 514/816
(58) Field of Search .................................. 424/725, 732, 424/777; 514/816

(56) References Cited

FOREIGN PATENT DOCUMENTS

| JP | 07101836 | * | 4/1995 |
| RO | 113712 | * | 10/1998 |

OTHER PUBLICATIONS

Hirschhorn, H. The Home Herbal Doctor. 1982. Publ: Perker Publishing Co., Inc. NY; pp. 52–53.*
Internet publication titled "Sanbucol Black Elderberry Extract—The Original Nature'Way" at www.betterlife.com; first published on internet in 1996, 2 pages.*
Internet publication titled "Elixir of Elderberry" at http://www.mothernature.com; first published on internet in 1995, 2 pages.*
Internet publication titled "Sambucol Black Elderberry" at http://www.mothernature.com; first published on internet in 1995, 2 pages.*
Keville, K. Vegetarian times. 1990. No. 154, pp. 62–65.*
Brown, Jr, T. Tom Brown's Guide to Wild Edible and Medicinal Plants. 1985. Publ: Berkely Brooks, NY; pp. 114–117.*

* cited by examiner

Primary Examiner—Christopher R. Tate
(74) Attorney, Agent, or Firm—Lynn Schwenning Alticor Inc.

(57) ABSTRACT

The present invention describes food supplements that contain one or more fruit extracts useful for pain relief and anti-inflammation. The food supplements may be used to inhibit inflammation mediated by cyclooxygenase and more particularly by cyclooxygenase-2.

15 Claims, 5 Drawing Sheets

DIETARY FOOD SUPPLEMENT CONTAINING NATURAL CYCLOOXYGENASE INHIBITORS AND METHODS FOR INHIBITING PAIN AND INFLAMMATION

RELATED APPLICATIONS

The present application is a continuation-in-part of PCT application Ser. No. PCT/US00/23423 filed Aug. 25, 2000, of U.S. Provisional Application Ser. No. 60/151,280 filed Aug. 27, 1999 and U.S. Provisional Application Ser. No. 60/151,278 filed Aug. 27, 1999, all of which are herein incorporated by reference.

BACKGROUND

The present invention relates to dietary food supplements that are useful for the relief of pain or inflammation, and also for the inhibition of biochemical pathways related to pain or inflammation transmission. These food supplements contain flavonoids, and more particularly, certain anthocyanins.

Today, many consumers seek natural alternatives to synthetic pharmaceutical products to aid with a variety of ailments experienced during daily life. Thus, dietary food supplements containing natural substances such as St. Johns wort, gingko biloba, ginseng, and others have recently been marketed for a variety of purposes. To date, however, it is believed that no product containing natural substances is available to provide for the relief of pain and/or inflammation equivalent to non-steroidal anti-inflammatory drugs ("NSAIDs").

At the present, pain and inflammation are commonly treated by the use of aspirin, ibuprofen (Motrin®, Advil®), and other similar substances commonly known as NSAIDs. Inflammation is transmitted, in part, by a class of compounds known as prostaglandins, which are released by a host in response to mechanical, thermal, chemical, bacterial, and other insults (Moncada et al., Handbook of Exp. Pharm. Vol 50-1, Springer Verlag, pp 588–616, 1978; Samuelsson, Science, 220: 568–575, 1983; Davies et al, Ann. Rev. Immunol. 2:335–357, 1984). Prostaglandin synthesis is accomplished in a stepwise manner by a ubiquitous complex of microsomal enzymes. The first enzyme in this biosynthetic pathway is prostaglandin endoperoxide synthase. This enzyme also is referred to in the art as fatty acid cyclooxygenase. There are two isoforms of this enzyme known as cyclooxygenase-1 (COX-1) and cyclooxygenase-2 (COX-2), respectively (Smith, Am. J. Physiol., 268:F181–F191, 1992).

Although substances such as aspirin inhibit prostaglandin production and thus, pain and/or inflammation, they may cause stomach problems and or ulcers. To address these problems, drugs have been developed to target specific pain pathways in the hope that some of the problems associated with aspirin, ibuprofen, and other similar substances will be reduced if not completely eliminated. One such drug is Celebrex™, which apparently targets a specific pain pathway and thus, does not have some of the disadvantages associated with substances such as aspirin. In particular, NSAIDs prevent the production of prostaglandins by inhibiting enzymes in the human arachidonic acid/prostaglandin pathway. Drugs like Celebrex™, however, distinguish between COX-1 and COX-2 and are touted as having less of the side effects associated with normal NSAIDs.

As noted above, many consumers prefer natural substances to synthetic drugs. Therefore, it is clear that there is a need for a natural and pharmacologically acceptable composition for use in relieving or alleviating pain, inflammation, and the symptoms associated with these conditions. In addition, there is a need for a natural composition that provides relief from pain and inflammation with minimal side effects to the gastrointestinal system. The present invention addresses that need by providing a dietary food supplement containing an extract from one or more anthocyanin-containing plants having a native active fraction that provides pain relief, anti-inflammation activity, and/or preferential COX-2 inhibition. The supplement contains an amount of the fraction in a proportion by dry weight of other components that significantly exceeds a proportion of the fraction present by dry weight in juice obtained from the plant material. In general, the active fraction includes flavonoids, and in particular, anthocyanins.

Unless otherwise specifically stated, all percentages used in the specification and claims are weight percentages.

DETAILED DESCRIPTION OF THE INVENTION

Figure 1:
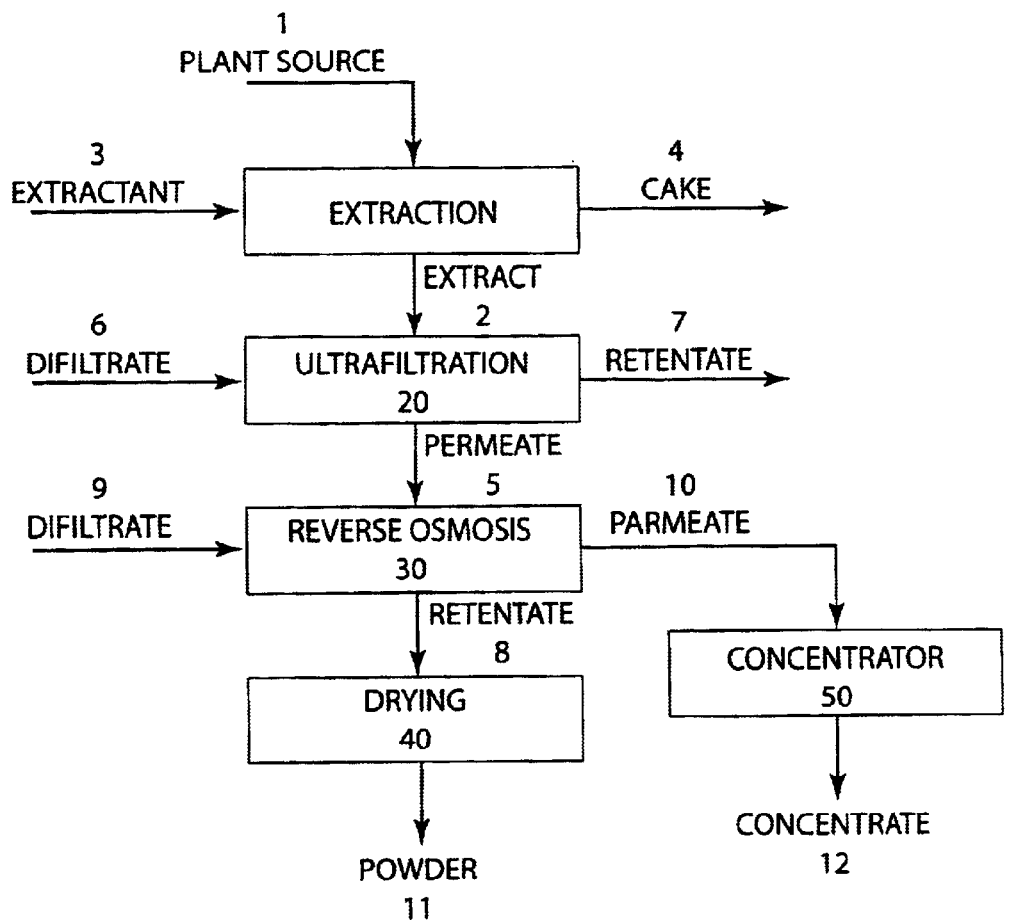
FIG. 1 shows a flow sheet of one embodiment of a process for obtaining and concentrating desirable anthocyanins from anthocyanin-containing plants.

Prostaglandins (which include $PGE_2$, $PGD_2$, $PGF_2$, $PGI_2$ and other related compounds) represent a diverse group of autocrine and paracrine hormones that are derived from the metabolism of fatty acids. They belong to a family of naturally occurring eicosanoids (prostaglandins, thromboxanes and leukotrienes) that are not stored as such in cells, but are biosynthesized on demand from arachidonic acid, a 20-carbon fatty acid that is derived from the breakdown of cell-membrane phospholipids. Under normal circumstances, the eicosanoids are produced at low levels to serve as important mediators of many and diverse cellular functions which can be very different in different types of cells. The prostaglandins, however, also play critical roles in pathophysiology. In particular, inflammation is both initiated and maintained, at least in part, by the overproduction of prostaglandins in injured cells. The central role that prostaglandins play in inflammation is underscored by the fact that those aspirin-like non-steroidal anti-inflammatory drugs (NSAIDS) that are most effective in the therapy of many pathological inflammatory states all act by inhibiting prostaglandin synthesis. Unfortunately, the use of these drugs is often limited by the side effects (gastrointestinal bleeding, ulcers, renal failure, and others) that result from the undesirable reduction in prostaglandins in normal cells that now suffer from a lack of those autocrine and paracrine functions that are required for the maintenance of normal physiology. The development of new agents that will act more specifically by achieving a reduction in prostaglandins in inflamed cells without altering prostaglandin production in other cells is a goal for future pain and inflammation therapy.

The cyclooxygenase reaction is the first step in the prostaglandin synthetic pathway; an enzyme (PGHS) with prostaglandin G/H synthetic activity converts arachidonic acid into the endoperoxide $PGG_2$, which then breaks down to $PGH_2$ (the two reactions are carried out by a single enzyme). $PGH_2$ is in turn metabolized by one or more prostaglandin synthase ($PGE_2$ synthase, $PGD_2$ synthase etc.) to generate the final "2-series" prostaglandins, $PGE_2$, $PGD_2$, $PGF_2$, $PGI_2$ and others that include the thromboxanes, $TXA_2$. The first step (PGHS) is the one that is rate-limiting for prostaglandin synthesis. As such, the PGHS-mediated reaction is the principal target for anti-inflammatory drug action; and it is inhibition of PGHS activity that accounts for the activity of the NSAIDS (aspirin, acetominophen, ibuprofen, naproxen, indomethacin) and others that limit the overproduction of prostaglandins in inflammation (the desired therapeutic goal) and reduce the normal production of prostaglandins in uninflamed cells (which produces the undesirable side effects).

In addition to the abnormal changes associated with inflammation, multiple other factors are known to influence prostaglandin production under experimental conditions. These include growth factors, cAMP, tumor promoters, src activation and interleukins 1 and 2, all of which increase overall cellular PGHS activity. The adrenal glucocorticoid honmones and related synthetic anti-inflammatory steroids also inhibit prostaglandin synthesis, but their metabolic site of action is not well defined.

The primary and perhaps sole action of most non-steroidal anti-inflammatory agents is to inhibit the enzyme prostaglandin G/H synthase, also known as cyclooxygenase, which serves as the first committed step in the biosynthesis of prostaglandins.

It is well established that cyclooxygenase exists in two isoforms, COX-1 and COX-2. The constitutively expressed form, COX-1, has been extensively studied and proposed to be involved in the maintenance of prostaglandin mediated physiological functions. In contrast, COX-2, the inducible form, is present in negligible amounts under normal conditions but is substantially induced in vivo under inflammatory conditions. Clearly, COX-1 and COX-2 serve different physiological and pathological functions.

The most widely available NSAIDs are non-selective cyclooxygenase inhibitors, inhibiting both isoforms indiscriminately. When dual inhibitor NSAIDs (NSAIDs that inhibit both the COX-1 and COX-2 enzymes) are used long-term to relieve pain and/or inflammation, the risk of developing gastrointestinal complications is moderate to high. Selective COX-2 inhibitors have been sought ever since it was discovered that the enzyme has two distinct isoforms. More recently, COX-2 specific inhibitors have been developed but it has been suggested that they too have side effects. In view of the above, there remains a need for a safe and effective method of treating pain and inflammation with minimal gastrointestinal side effects. The present invention addresses such a need.

The present invention describes a natural alternative to NSAIDs that preferentially inhibits for COX-2 activity and ameliorates inflammation and pain mediated by COX-2 while remaining gentle on the stomach and intestines. The invention shows that extracts or other concentrated forms of certain anthocyanin-containing plants possess an anti-inflammatory activity greater than the anti-inflammatory activity found in the natural plant. This observation is exploited to provide a food supplement that comprises an extract having an anti-inflammatory activity greater than the anti-inflammatory activity found in the natural plant and a pharmaceutically acceptable diluent or excipient. In other words, the present invention provides extracts obtained from anthocyanin-containing plants, particularly fruits, to provide selective COX-2 inhibition.

Alternatively, extracts from anthocyanin-containing plants may selectively inhibit activity of COX-1. Studies have indicated that some COX-1 inhibition in a pain and/or anti-inflammatory medication provides a beneficial effect to the cardiovascular system.

Accordingly, the present invention contemplates a food supplement that contains at least one anthocyanin derived from an extract of an anthocyanin-containing plant to selectively inhibit activity of COX-1 or COX-2. As used herein, the term "extract" includes any preparation obtained from plant, fruit, and vegetable using different extraction methods.

A. Identification of Anthocyanin-containing Sources

There is a growing need for dietary supplements that contain beneficial phytochemicals that are naturally found in plants. These naturally occurring phytochemicals can be classified in several different groups. One of the more important groups is the flavonoids, which in turn, can be classified into several groups. One important group of flavonoids is the anthocyanins. Anthocyanins are most prevalent in the flowers and fruits that are red, blue, and intermediate colored such as cherries (sweet, sour (or tart)), acerola cherry, blue plums, bilberry, blackberry, currant, chokeberry, blueberry, strawberry, cranberry, boysenberry, grapes, raspberry, and elderberry.

The anthocyanins may be obtained from any portion of the plant, including, but limited to, the fruit, flower, stem, leaves, root, bark, and seeds. One of skill in the art, however, will understand that certain portions of the plant may contain higher natural levels of anthocyanins and therefore those portions will be used to obtain the desired anthocyanins. Methods to determine whether and which portions of a plant contains anthocyanins are known and therefore, not discussed here.

Examples of suitable anthocyanin-containing plants include fruits, vegetables, flowers and other plants selected from the group consisting of *Acer macrophyllum, Acer platanoides*, acerola, *Ajuga reptans*, apple, apricot, Artict bramble, avocado, banana, barberry, barley, *Begonia semperflorens, Bellis perennis, Bletilla striata*, bilberry, black beans, black soybeans, black, blue and purple potatoes, blackberry, blueberry, bog whortleberry, boysenberry, buckwheat, cacao, *Camellia sinensis*, canarygrass, Caucasian blueberry, *Chimonanthus praecox*, celery, *Cerasus avium*, cherry, cherry laurel, chicory, chive, chokeberry, Cornelian cherry, cornflower, cotoneaster, cowberry, cranberry, crowberry, chrysanthemum, *Cynomorium coccineum, Dahlia variabilis*, danewort, deerberry, Dendrobium, dwarf dogwood, Echinacea purpea, eggplant, elderberry, fababean, *Fatsia japonica*, feijoa, fig, garlic, gerbera, ginseng, Globe artichoke, gooseberry, grapes, guava, hawthorn, hibiscus or roselle, *Hibiscus Sabdaiffa*, highbush blueberry, hollyhock, honeysuckle, *Ipomoea purpurea, Iris ensata*, Java plum, Jerusalem artichoke, kokum, Laeliocattleya spp, lentil, loganberry, lupine, lychee, maize, mango, mangosteen, maqui, *Matthiola incana*, meconopsis, *Metrosideros excelsa*, millet, mountain ash berry, mulberry, myrtle berry, olive, onion, orange, ornamental cherry, passion fruit, pea, peach, peanut, pear, perilla, petunia, Phalaenopsis spp. Phalsa, Pharbitis spp. Pineapple, pistachio, plum, pomegranate, *Phragmites australis*, purple carrot, quince, rabbiteye blueberry, radish, red and black currant, red and black raspberry, red cabbage, rice, rhubarb, rosehip, rye, saffron, sarracenia, sheepberry, Sophronitis coccinea, sorghum, sparkleberry, strawberry, *Fragada Vesca*, sugarcane, sunflower, sweet cherry, sweet potato, tamarillo, tamarind, taro, tart cherry, *Tulip greigii*, turnip, water lily, Weigela spp, wheat, wild rice, *Verbena hybrida*, yam and mixtures thereof.

The chemistry of anthocyanins is based on 2-phenylbenzopyrylium (flavylium) having the following structure:

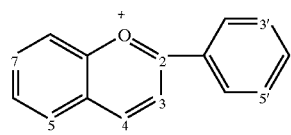

If this basic formula is substituted with hydroxy or methoxy groups at 2, 3, 4, 5, 7, 3' or 5', the resultant compounds are known as anthocyanidins, which are water insoluble, unstable to light and rapidly destroyed by alkali and thus not found too often in plants. Table 1 below shows the structure for several of the anthocyanidins:

TABLE 1

| Name | \multicolumn{7}{c}{Substitution Pattern} | Color |
|------|---|---|---|---|----|----|----|-------|
|      | 3 | 5 | 6 | 7 | 3' | 4' | 5' |       |
| Cyanidin (Cy) | OH | OH | H | OH | OH | OH | H | Orange red |
| Delphinidin (Dp) | OH | OH | H | OH | OH | OH | OH | Bluish-red |
| Malvidin (Mv) | OH | OH | H | OH | OME | OME | OME | Bluish-red |
| Pelargonidin (Pg) | OH | OH | H | OH | H | OH | H | Orange |
| Peonidin (Pn) | OH | OH | H | OH | OME | OH | H | Orange-red |
| Petunidin (Pt) | OH | OH | H | OH | OME | OH | OH | Bluish-red |

Anthocyanins are the glycosides of the above compounds and are more stable and found as native substances in the leaves, flowers and fruits of plants. The anthocyanins may be hydrolyzed to produce anthocyanidins (the aglycone form) and sugars.

The total number of anthocyanins found in nature is extremely large, since many mono, di and tri-saccharides may be glycosylated at the 3, 5 or 7 positions and also since the sugar at position 3 may be acylated (often with p-coumaric acid). Thus, a particular fruit may have 20 or more anthocyanins including the 3,5-diglucosides, the 3-mono-glucoside, the 3-(6-O-p-coumaryl-glucoside)-5-glucosides and the 3-(6-O-p-coumaryl-glucoside) of cyanidin, delphinidin, petunidin, pelargonidin and malvidin. The color of anthocyanins is determined by their molecular structure and the physiochemical nature of the medium in which they are present.

In accordance with the present invention, the extract contains one or more anthocyanins and anthocyanidins selected from the group consisting of peonidin, cyanidin, pelargonidin, delphinldin, petunidin, malvidin, apigenindin, auratinidin, capensinidin, europinidin, hirsutidin, 6-hydroxycyanidin, luteolinidin, 5-methylcyanidin, pulchellidin, rosinidin, tricetnidin, derivatives and mixtures thereof. In one embodiment, the anthocyanins and anthocyanidins are selected from the group consisting of cyanidin, peonidin, malvidin, petunidin, delphinidin, their glycoside derivatives, and mixtures thereof. In yet another embodiment, the extract contains at least one cyanidin-based anthocyanin.

Anthocyanins that may be useful in the inventions described herein include, but are not limited to, cyanidin-3-glucoside; cyanidin 3-glucosylrutinoside; cyanidin-3-gentibioside; cyanidin-3-rutinoside, cyanidin-3-sambunigrin, cyanidin-3-samb-5-glucoside, cyanidin-3-galactoside, peonidin-3-rutinoside, peonidin-3-glucoside, peonidin-3-galactoside, peonidin, cyanidin, cyanidin-3 sophoroside, pelargonidin, delphinidin, delphinidin-3-glucoside, delphinidin-3-galactoside, petunidin, petunidin-3-glucoside, petunidin-3-galactoside, malvidin, malvidin-3-arabinoside, malvidin-3-glucoside, malvidin-3-galactoside, kaempferol, hesperidin, gentiodelphin, platyconin, cinerarin and the like.

It has been found that hydrolyzed anthocyanins (i.e. anthocyanidins) may provide greater COX inhibition activity as compared to the anthocyanin and its glycoside derivatives. It is believed that the anthocyanins provide little, if any, COX inhibition, particularly COX-1 inhibition. However, it has also been found that it may be advantageous to include anthocyanins in the dietary food supplement and allow them to be hydrolyzed in vivo to the anthocyanidin form. It is believed that the anthocyanins can be absorbed or passed through the gastrointestinal tract without inhibiting the COX 1 enzyme there. As a result, the amount of prostaglandins generated by the COX 1 enzyme on the gastrointestinal tract remains normal or high enough to maintain the GI lining. After the absorption, the sugar moieties are cut off and the active form, the anthocyanidins, are transported to the sites where the COX 2 enzymes are being induced, thereby inhibiting the COX 2 enzymes and providing relief from pain and inflammation. As a result, the present invention is believed to provide an advantage over currently available COX inhibitors, such as NSAIDs, since there will be little inhibition of the COX-1 in the gastrointestinal tract, with a possible reduction in side effects.

As described further in the Examples, cyanidin may provide a greater amount of COX inhibition as compared to the other anthocyanidins. Accordingly, it may be desirable to provide a dietary supplement having a high concentration of cyanidin-based anthocyanins to achieve pain and inflammation relief. It has further been found that anthocyanins containing only a single sugar moiety may provide a greater amount of COX inhibition as compared to di-saccharchide, tri-saccharide, or other multiple saccharide anthocyanins. Table 2 identifies the cyanidin-based, mono-saccharide anthocyanins found in many natural sources.

TABLE 2

| Anthocyanin-containing plant | Latin Name | Commercial source of an extract or other concentrated product | Cyanidin-based anthocyanins found In this source[1] Weight percentage, if provided, is relative to all known anthocyanins in this source | Cyanidin-based mono-saccharides found in this source | COX1/COX2 Ratio[2] |
|---|---|---|---|---|---|
| | Acer macrophyllum | N/A | Cyanidin derivative | N/A | N/A |
| | Acer platanoides | N/A | Cyanidin 3-(2",3"-digalloyl-beta-glucopyranose (3%) Cyanidin 3-(2"-galloyl-beta-glucopyranose (37%) Cyanidin 3-beta-glucopyranoside (60%) | N/A | N/A |
| Acerola | Malpighia marginata | N/A | Cyanidin-3-glucoside | Cyanidin-3-glucoside | N/A |
| | Ajuga reptans | N/A | Cyanidin 3-(di-p-coumaroyl) sophoroside-5-glucoside | N/A | N/A |
| Apple | Malus spp | N/A | Cyanidin 3-galactoside Cyanidin 3-arabinoside Cyanidin 3-glucoside Cyanidin 3-xyloside | Cyanidin 3-galactoside Cyanidin 3-arabinoside Cyanidin 3-glucoside Cyanidin 3-xyloside | N/A |
| Apricot | Prunus armeniaca | N/A | Cyanidin-3-glucoside | Cyanidin-3-glucoside | N/A |
| Artic bramble | Rubus spp | N/A | N/A | N/A | N/A |
| Avocado | Persea spp | N/A | Acylated cyanidin 3,5-diglucoside Cyanidin 3-galactoside | Cyanidin 3-galactoside | N/A |
| Banana | Musa acuminata M. balbisiana | N/A | N/A | N/A | N/A |
| Barberry | Berberis spp. | N/A | Cyanidin-glucoside | Cyanidin-glucoside | N/A |
| Barley | Hordeum vulgare | N/A | Cyanidin and cyanidin glycosides | N/A | N/A |
| Bean | Pheseolus vulgaris (several cultivars) | N/A | Cyanidin 3-glucoside Cyanidin 3,5-diglucoside | Cyanidin 3-glucoside | N/A |
| | Begonia semperflorens cvs | N/A | Cyanidin derlvatfve | N/A | N/A |
| Benibana-cha | Camellia sinensis | N/A | Cyanidin 3-O-beta-D galactoside | Cyanidin 3-O-beta-D-galactoside | N/A |
| | Bellis perennis | N/A | 3 Cyanidin 3-derivatives | N/A | N/A |
| | Bletilla striata | N/A | Acylated cyanidin 3,7,3'-triglucoside derivatives | N/A | N/A |
| Bilberry | Vaccinium myrtillus | Artemis/Iprona; Indena | Cyanidin-3-galactoside (22%); Cyanidin-3-glucoside (9%) | Cyanidin-3-galactoside Cyanidin-3-glucoside | >1.3 |
| Black beans | Phaseolus | N/A | Cyanidin-3-glucoside (96%) | Cyanidin-3-glucoside | N/A |
| Blackberry (European and American) | Moriferi veri Rubus caesius R. alleghniensis, R. argufus, R. cuneifolius, R. setosus, R. trivials. | N/A | Cyanidin-glucoside (70-100%) Cyanidin-rutinoside | Cyanidin-glucoside | N/A |
| Black grapes | Many varieties | N/A | N/A | N/A | N/A |
| Black potatoes | Solanum tuberosum | N/A | Cyanidin-glycosides* | | N/A |
| Black raspberry | Rubus occidentalis | N/A | Cyanidin-sambubloside (20%); Cyanidin-xylosylrutinoside (40%); Cyanidin-glucoside (17%) Cyanidin-rutinoside (23%) | Cyanidin-sambubloside Cyanidin-glucoside | >1.3 |
| Black soybeans | Glycine max | N/A | Cyanidin-3-glucoside (96%) | Cyanidin-3-glucoside | N/A |

TABLE 2-continued

| Anthocyanin-containing plant | Latin Name | Commercial source of an extract or other concentrated product | Cyanidin-based anthocyanins found In this source[1] Weight percentage, if provided, is relative to all known anthocyanins in this source | Cyanidin-based mono-saccharides found in this source | COX1/COX2 Ratio[2] |
|---|---|---|---|---|---|
| Blueberries | Five common Vaccinium spp | N/A | Cyanidin-glucoside (3%); Cyanidin-galactoside (3%); Cyanidin-arabinoside (3%) | Cyanidin-glucoside Cyanidin-galactoside Cyanidin-3-arabinoside | N/A |
| Bog whortleberry | *Vaccinium uliginosum* | N/A | Cyanidin 3-glucoside (14%) Cyanidin #arabinoside (10%) Cyanidin 3-galactoside (6.5%) | Cyanidin 3-glucoside (14%) Cyanidin 3-arabinoside (10%) Cyanidin 3-galactoside (6.5%) | |
| Boysenberry | | new Zealand | Cyanidin-3-sophoroside (44.5%) Cyanadin-3-glucoside (26.4%); Cyanidin-3-glycosylrutinoside (25.8%); Cyanidin-rutinoside (3.3%) | Cyanidin-3-glucoside | N/A |
| Buckwheat | *Fagopyrum species* | N/A | Cyanidin 3-glucoside Cyanidin 3-galactoside | Cyanidin 3-glucoside Cyanidin 3-galactoside | N/A |
| Cacao | *Theobroma cacao* | N/A | Cyanidin 3-glucoside (suspected) | Cyanidin 3-glucoside (suspected) | N/A |
| Celery | Apium spp | N/A | N/A | N/A | N/A |
| Cherry laurel | *Prunus laurocerasus* | N/A | Cyanidin 3-arabinoside | Cyanidin 3-arabinoside | N/A |
| Chicory | *Cichorium intybus* | N/A | Cyanidin 3-glucoside | Cyanidin 3-glucoside | N/A |
| Chive | *Allium schoenoprasum* | N/A | Cyanidin 3-glucoside Cyanidin 3-acetylglucoside Cyanidin 3-(6-malonylglucoside) Cyanidin 3-(3,6-dimalonylglucoside) | Cyanidin 3-glucoside | N/A |
| Chokeberry | *Aronia melanocarpa* | Artemis/lprona | Cyanidin-3-galactoside (64.5%); Cyanidin-3-arabinoside (28.9%); Cyanidin-3-glucoside (2.4%); Cyanidin-3-xyloside (4.2%) | Cyanidin-3-galactoside Cyanidin-3-arabinoside Cyanidin-3-glucoside Cyanidin-3-xyloside | >1.3 |
| Coffee | *Coffea arabica* cv. Bourbon Vermelho | N/A | Cyanadin 3-glycoside Cyanadin 3,5-diglycoside | Cyanadin 3-glycoside | N/A |
| Cotoneaster | Cotoneaster Medic. Spp.) | N/A | Cyanidin 3-glucoside Cyanidin 3-galactoside Cyanidin 3-rutinoside | Cyanidin 3-glucoside Cyanidin 3-galactoside | N/A |
| Cowberry or Lingonberry | *V. vitis-idaea* | N/A | Cyanidin 3-galactoside Cyanidin 3-arabinoside Cyanidin 3-glucoside | Cyanidin 3-galactoside Cyanidin 3-arabinoside Cyanidin 3-glucoside | N/A |
| | *Chimonanthus praecox* | N/A | Cyanidin 3-O-glucoside Acylated cyanidin 3-O-glucoside Cyanidin glycoside | Cyanidin-3-O glucoside | N/A |
| Cranberry (American and European) | *Vaccinium macrocarpon V. oxycoccus* | Ocean Spray | Cyanidin-galactoside (16–24%) Cyanidin-arabinoside (13–25%) | Cyanidin-galactoside Cyanidin-arabinoside | N/A |
| Crowberry | *Empetrum nigrum* | N/A | Cyanidin 3-glucoside Cyanidin 3,5-diglucoside Cyanidin 3-rutinoside Cyanidin 3-sophoroside | Cyanidin 3-glucoside | N/A |

TABLE 2-continued

| Anthocyanin-containing plant | Latin Name | Commercial source of an extract or other concentrated product | Cyanidin-based anthocyanins found In this source[1] Weight percentage, if provided, is relative to all known anthocyanins in this source | Cyanidin-based mono-saccharides found in this source | COX1/COX2 Ratio[2] |
|---|---|---|---|---|---|
| Chrysanthemum | Dendranthema Grandiflorum | N/A | Cyanidin 3-O-(6'-O-malonyl-beta-glucopyranoside | N/A | N/A |
| Currant (red and black) | Ribes rubrum R. nigrum | N/A | Cyanidin-glucoside (2–10%), Cyanidin-rutinoside (8–17%), Cyanidin-sambubioside (9–31%), Cyanidin-sophoroside (4–9%), Cyanidin-xylosylrutinoside (28–73%) Cyanidin-glucosylrutinoside (14–28%) | Cyanidin-glucoside, Cyanidin-sambubioside | N/A |
|  | Cynemonurn coccineum | N/A | Cyanidin 3-O-glucoside (92%) Cyanadin 3-O-(6-O-rhamnosylglucoside (8%) | Cyanidin 3-O-glucoside (92%) | N/A |
| Danewort | Sambucus ebulus | N/A | Cyanidin 3-xylosylglucoside Cyanidin 3-sambubioside Cyanidin 3-sambubloside-5-glucoside Cyanidin 3,5 diglucoside Cyanidin 3-glucoside Cyanidin 3-arabinoglucoside | Cyanidin 3-sambubioside Cyanidin 3-glucoside | N/A |
| Dendrobium | Phalaenapsis spp | N/A | Cyanidin derivatives | N/A | N/A |
| Dwarf dogwood | Cornus suecica | N/A | Cyanidin 3-glucoside (4%) Cyanidin 3-galactoside (16%) 2 Cyanidin derivatives (80%) | Cyanidin 3-glucoside (4%) | N/A |
| Echinacea | Echinacea spp. | N/A | N/A | N/A | N/A |
| Eldenberry | Sambucus nigra | Artemis/lprona | Cyanidin-3-glucoside (42%) Cyanidin-3-sambubioside (43%) Cyanidin-3,5-diglucoside (2%) Cyanidin-3-sambubloside-5-glucoside (9%) | Cyanidin-3-glucoside | >1.3 |
|  | Gentiana spp | N/A | Cyanidin 3-O-beta-D-glucoside and 3 other derivatives | Cyanidin 3-O-beta-D-glucoside | N/A |
|  | Fatsia japonica | N/A | Cyanidin 3-lathyroside | N/A | N/A |
| Feijoa | Feijoa sellowiana | N/A | Cyanidin 3-glucoside | Cyanidin 3-glucoside | N/A |
| Fig | Ficus carica spp | N/A | Cyanidin 3-rhamnoglucoside Cyanidin 3,5-diglucoside Cyanidin 3-glucoside | Cyanidin 3-glucoside | N/A |
|  | Forsythia X intermedia cv Spring Glory | N/A | Cyanidin derivatives | N/A | N/A |
| Garlic | Allium sativum | N/A | Cyanidin 3-glucoside Cyanidin 3-glucoside monoacylated Cyanidin 3-glucoside triacylated | Cyanidin 3-glucoside | N/A |
| Ginseng | Panax ginseng Panax quinquefolius | N/A | Cyanidin 3-O-β-D-xylopyranyl-(1-2)-β-D-glucopyranoside | N/A | N/A |

TABLE 2-continued

| Anthocyanin-containing plant | Latin Name | Commercial source of an extract or other concentrated product | Cyanidin-based anthocyanins found In this source[1] Weight percentage, if provided, is relative to all known anthocyanins in this source | Cyanidin-based mono-saccharides found in this source | COX1/COX2 Ratio[2] |
|---|---|---|---|---|---|
| Globe artichoke | Cynara scolymus | N/A | Cyanidin 3-caffeylglucoside Cyanidin 3-caffeylsophoroside Cyanidin 3-dicaffeylsophoroside | N/A | N/A |
| Gooseberry | Ribes spp | N/A | Cyanidin 3-glucoside Cyanidin 3-rutinoside | Cyanidin 3-glucoside | N/A |
| Grape | Vinis vinifera | N/A | Cyanidin 3-monoglucoside Cyanidin 3-monoglucoside-acetate Cyanidin 3-monoglucoside-p-coumarate | Cyanidin 3-monoglucoside | N/A |
| Guava | Psidium guajavica | N/A | Cyanidin 3-glucoside | Cyanidin 3-glucoside | N/A |
| Hawthorn | Crataegus spp | N/A | Cyanidin 3-galactoside Cyanidin 3-arabinoside Cyanidin 3-glucoside | Cyanidin 3-galactoside Cyanidin 3-glucoside | N/A |
| Hibiscus or Roselle | Hibiscus sabdariffa | N/A | Cyanidin-sambubioside (30%) | Cyanidin-sambubioside | N/A |
| Hollyhock | Althaea rosea | N/A | Cyanidin 3-glucoside Cyanidin 3-rutinoside Other cyanidin glucosides | Cyanidin 3-glucoside | N/A |
| Honeysuckle | Lonicera nitida | N/A | Cyanidin 3-rutinoside Cyanidin 3-glucoside | Cyanidin 3-glucoside | N/A |
| Japanese garden iris | Iris ensata | N/A | Cyanidin 3RG Cyanidin 3RG5G Cyanidin 3Rgac5G | N/A | N/A |
| | Ipornoea purpurea | N/A | Six acylated cyanidin 3-sophoroside-5-glucosides | N/A | N/A |
| Java plum | Myrciana jaboticaba | N/A | Cyanidin 3-glucoside | Cyanidin 3-glucoside | N/A |
| Jerusalem artichoke | Helianthus tuberosus | N/A | N/A | N/A | N/A |
| Kokum | Garcinia indica | N/A | Cyanidin 3-glucoside Cyanidin 3-sambubioside | Cyanidin 3-glucoside Cyanidin 3-sambubioside | N/A |
| | Laeliocattleya cv Mini purple | N/A | Acylated cyanidin derivatives | N/A | N/A |
| | Lactuca sativa | N/A | Cyanidin 3-O-(6"-malonylglucoside) | N/A | N/A |
| Loganberry | Rubus loganbaccus | N/A | Cyanidin-sophoroside (48.1 %), Cyanidin-glucoside (21.6%), Cyanidin-rutinoside (6.2%) | Cyanidin -glucoside | N/A |
| Lupine | Lupinus spp | N/A | Cyanidin glycosides presence confirmed | N/A | N/A |
| Lychee | Litchi chinensis | N/A | Cyanidin 3-glucoside Cyanidin 3-galactoside Cyanidin 3-rutinoside | Cyanidin 3-glucoside Cyanidin 3-galactoside | N/A |
| Maize | Zea mays | N/A | Cyanidin 3-glucoside Cyanidin 3-(6"-malonylglucoside) Cyanidin 3-(3",6"dimalonyl-glucoside) | Cyanidin 3-glucoside | N/A |
| Mango | Mangifera indica | N/A | Cyanidin glycosides | N/A | N/A |
| Mangosteen | Garcina mangostana | N/A | Cyanidin 3-sophoroside Cyanidin 3-glucoside | Cyanidin 3-glucoside | N/A |

TABLE 2-continued

| Anthocyanin-containing plant | Latin Name | Commercial source of an extract or other concentrated product | Cyanidin-based anthocyanins found In this source[1] Weight percentage, if provided, is relative to all known anthocyanins in this source | Cyanidin-based mono-saccharides found in this source | COX1/COX2 Ratio[2] |
|---|---|---|---|---|---|
| Maqul | *Aristotella chilensis* | N/A | Cyanidin 3-,5-diglucoside | N/A | N/A |
| | *Matthiola incana* | N/A | Four acylated cyanidin 3-sambubloside-5-glucosides | N/A | N/A |
| Millet | *Pennisetum americanum* | N/A | Cyanidin 3-glucoside | Cyanidin 3-glucoside | N/A |
| Mountain ash berry | *Sorbus spp* | N/A | Cyanidin 3-galactoside Cyanidin 3,5-diglucoside Cyanidin 3-β-D-glucopyranoside | N/A | N/A |
| Mulberry | *Morus nigra* | N/A | Cyanidin 3-glucoside Cyanidin 3,5-diglucoside Cyanidin 3-rutinoside Cyanidin 3-sophoroside | Cyanidin 3-glucoside | N/A |
| Myrtle berry | *Myrtus communis* | N/A | Cyanidin 3-glucosides Cyanidin 3,-diglucosides | Cyanidin 3-glucosides | N/A |
| Olive | *Olea europaea* | N/A | Cyanidin 3-rutinoside Cyanidin 3-glucoside Cyanidin derivatives | Cyanidin 3-glucoside | N/A |
| Onion | *Allium sepa* | N/A | Cyanidin 3-glucoside Cyanidin 3-diglucoside Cyanidin 3-laminarioside | Cyanidin 3-glucoside | N/A |
| Orange | *Citrus sinensis* | N/A | Cyanidin 3-glucoside (95%) Cyanidin 3,5-diglucoside | Cyanidin 3-glucoside | N/A |
| Passion fruit | *Pasiflora edulis* | N/A | Cyanidin 3-glucoside | Cyanidin 3-glucoside | N/A |
| Pea | *Pisum sativum* | N/A | Cyanidin 3-sophoroside glucosides Cyanidin 3-sambubioside-5-glucosides | N/A | N/A |
| Peach | *Prunus persica* | N/A | Cyanidin 3-glucoside Cyanidin 3-rutinoside Cyanidin derivatives | Cyanidin 3-glucoside | N/A |
| Peanut | *Arachis hypogaea* | N/A | Cyanidin glucosides | N/A | N/A |
| Pear | *Pyrus communis* | N/A | Cyanidin 3-galactoside Cyanidin 3-arabinoside | Cyanidin 3-galactoside Cyanidin 3-arabinoside | N/A |
| Perilla | *Perilla frutescens* | N/A | Cyanidin 3,5-diglucoside Cyanidin 3,5-derivatives | N/A | N/A |
| | *Petunia spp* | N/A | Cyanidin 3-rutinoside | N/A | N/A |
| Phalsa | *Grewia spp* | N/A | Cyanidin 3-glucoside | Cyanidin 3-glucoside | N/A |
| Pineapple | *Anans comosus* | N/A | Cyanidin 3-galactoside | Cyanidin 3-galactoside | N/A |
| Pistachio | *Pistacia vera* | N/A | N/A | N/A | N/A |
| | *Pragmites australis* | N/A | Cyanidin-3 derivatives | N/A | N/A |
| Plum | 2000 varieties 15 species | N/A | Cyanidin-glucoside (37%) Cyanidin-rutinoside (45%) | Cyandin-glucoside | N/A |
| Pomegranate | *Punica granatum* | N/A | Cyanidin-glucoside (30%) Cyanidin-diglucoside (17%) | Cyanidin-glucoside | N/A |
| Purple carrot | *Daucus carota* | N/A | Cyanidin-glucoside Cyanidin-glucosylgalactoside Cyanidin-digalactoside Cyanidin-galactoside | Cyanidin-glucoside Cyanidin-galactoside | N/A |
| Quince | *Cydonia oblonga* | N/A | Cyanidin-3 glucoside Cyanidin 3,5-diglucoside Cyanidin derivatives | Cyanidin 3-glucoside | N/A |
| Radish | *Raphanus sativus* | N/A | Acylated cyanidin 3-sophoroside-5-glucoside Acylated cyanidin 3-diglucoside-5-glucoside | N/A | N/A |

TABLE 2-continued

| Anthocyanin-containing plant | Latin Name | Commercial source of an extract or other concentrated product | Cyanidin-based anthocyanins found In this source[1] Weight percentage, if provided, is relative to all known anthocyanins in this source | Cyanidin-based mono-saccharides found in this source | COX1/COX2 Ratio[2] |
|---|---|---|---|---|---|
| Red cabbage | Brassica oleracea var. capitata | N/A | Cyanidin glycosides* | N/A | N/A |
| Reed canarygrass | Phalaris arundinacea | N/A | Cyanidin 3-glucoside Cyanidin 3-(6"-malonylglucoside) Cyanidin 3-(3",6"dimalonyl-glucoside) | Cyanidin 3-glucoside | N/A |
| Red onion | Allium cepa | N/A | Cyanidin 3-glucoside Acylated cyanidin 3-glucoside derivatives | Cyanidin 3-glucoside | N/A |
| Red petunia | Petunia spp | N/A | Cyanidin 3-glucoside Cyanidin 3-sophoroside | Cyanidin 3-glucoside | N/A |
| Red raspberry | Rubus idaeus | N/A | Cyanidin glucoside (17%); Cyanidin-rutinoside (7%); Cyanidin-sophoroside (50%); Cyanidin-glycosylrutinoside (26%); Cyanidin-diglucoside | Cyanidin-glucoside | N/A |
| Rhubarb | Rneum spp | N/A | Cyanidin 3-glucoside Cyanidin 3-rutinoside | Cyanidin 3-glucoside | N/A |
| Rice | Oryza spp | N/A | Cyanidin 3-glucoside Cyanidin 3-rhamnoside Cyanidin 3,5-diglucoside | Cyanidin 3-glucoside | N/A |
| Rosehip | Rosa canina | N/A | Cyanidin 3-rutinoside Cyanidin 3-glucoside Cyanidin 3,5-diglucoside | Cyanidin 3-glucoside | N/A |
| Rye | Secale cereale | N/A | Cyanidin 3-glucoside Cyanidin 3-rhamnosylglucoside Cyanidin 3-rhamnosyldiglucoside Cyanidin 3-rutinoside Cyanidin 3-rutinoside derivatives Cyanidin 3-gentiobioside | Cyanidin 3-glucoside | N/A |
| Sheepberry | Vibumum spp | N/A | Cyanidin 3-glucoside Cyanidin 3-arabinosylsambubioside | Cyanidin 3-glucoside | N/A |
| Sorghum | Sorghum bicolor | N/A | Cyanidin Cyanidin glycosides | N/A | N/A |
| Sparkleberry | V. arboreum | N/A | Cyanidin 3-glucoside Cyanidin 3-arabinoside Cyanidin 3-galactoside | Cyanidin 3-glucoside | N/A |
| Strawberry | Fragaria ananassa | N/A | Cyanidin-glucoside(minor) | Cyanidin-glucoside | N/A |
| Sunflower | Hellanthus annuus | N/A | Cyanidin 3-glucoside Acylated cyanidin 3-glucoside Cyanidin 3-xyloside Acylated cyanidin 3-xyloside Cyanidin 3-vanillyl-sambubioside | Cyanidin 3-glucoside Cyanidin 3-xyloside | N/A |
| Sweet cherry | Prunus avium | N/A | Cyanidin-glucoside Cyanidin-rutinoside; Cyanidin-3-sophoroside | Cyanidin-glucoside | N/A |
| Sweet potato | Ipornoea batatas | N/A | Cyanidin derivatves | N/A | N/A |
|  | Sophronitis coccinea | N/A | Five acylated cyanidin 3,3',7-triglucosides | N/A | N/A |
| Tamarillo or tomato tree | Cyphomandrea betacea | N/A | Cyanidin 3-rutinoside Cyanidin 3-glucoside | Cyanidin 3-glucoside | N/A |
| Tamarind | Tamarindus indica | N/A | Cyanidin 3-glucoside | Cyanidin 3-glucoside | N/A |
| Taro | Colocasia esculenta | N/A | Cyanidin 3-glucoside Cyanidin 3-rutinoside | Cyanidin 3-glucoside | N/A |

TABLE 2-continued

| Anthocyanin-containing plant | Latin Name | Commercial source of an extract or other concentrated product | Cyanidin-based anthocyanins found In this source[1] Weight percentage, if provided, is relative to all known anthocyanins in this source | Cyanidin-based mono-saccharides found in this source | COX1/COX2 Ratio[2] |
|---|---|---|---|---|---|
| Tart Cherry (balaton) | *Prunus cerasus* cv. Balaton | Nutrilite | Cyanidin-3-rutinoside-hexose (75%); Cyanidin-3-rutinoside-pentose (3%); Cyanidin-3-rutinoside (18%); | N/A | >1.3 |
| Tart cherry (montmorency) | *Prunus cerasus* cv. Montmorency | Nutrilite | Cyanidin-3-sophoroside (80%); Cyanidin-3-glucoside (20%) | Cyanidin-3-glucoside (20%) | >1.3 |
| Tulip | *Tulipa spp* | N/A | Cyanidin 3-O-(6"-rhamnosylglucosides Cyanidin 3-O-derivative | N/A | N/A |
| Turnip | *Bressica rapa* | N/A | Cyanidin 3-glucoside Cyanidin 3-diglucoside-5-glucoside Cyanidin 3,5-diglucoside | Cyanidin 3-glucoside | N/A |
| Water lily | *Nymphasa alba* | N/A | Cyanidin 3-O-(6"-acetyl-beta-galactopyrosinase (23%) Cyanidin 3-O-galactoside (2%) | Cyanidin 3-O-galactoside (2%) | N/A |
|  | *Weigela spp* | N/A | Cyanidin 3-O-glucoside Cyanidin 3-O-glucoside xylose | Cyanidin 3-O-glucoside | N/A |
| Wheat | *Triticum spp* | N/A | Cyanidin 3-glucoside Acylated cyanidin glucoside Cyanidin 3-rutinoside Acylated cyanidin 3-rutinoside Cyanidin 3-gentiobioside | Cyanidin 3-glucoside | N/A |
| Wild rice | *Zizania aquatica* | N/A | Cyanidin 3-glucoside Cyanidin 3-rhamnoglucoside | Cyanidin 3-glucoside | N/A |
| Yam | *Dioscoracea spp* | N/A | Cyanidin 3,5-diglucoside Cyanidin 3-glucoside Cyanidin 3-rhamnoglucoside Cyanidin 3-gentiobioside Acylated cyanidin glucosides | Cyanidin 3-glucoside |  |

B. Methods for Extracting Anthocyanins

There are various method for the extraction of anthocyanins known to those of skill in thee art. Some of these methods are described in, for example, U.S. Pat. No. 5,817,354; U.S. Pat. No. 5,200,186; U.S. Pat. No. 5,912,363; U.S. Pat. No. 4,211,577; U.S. Pat. No. 4,302,200 (each incorporated herein by reference).

U.S. Pat. No. 5,817,354 describes a process for removing flavonoids from citrus products that cause the bitter taste. The process includes contacting a fluid containing one or more these bitter flavonoids with a polystyrene divinylbenzene resin to bind the flavonoids to the resin. Generally, a centrifugation or ultrafiltration step is used before contacting with the polystyrene divinylbenzene resin. The flavonoids can then be collected by eluting from the resin. While this patent does not describe how the flavonoids can be eluted (removed) from the resin, Chandra, et al. (J. Agric. Food Chem., 1062–64, Vol. 41, No. 7 (1993)) describe the use of ethanol to elute the anthocyanins. The eluted solution is then vacuum dried to remove the ethanol.

U.S. Pat. No. 5,912,363 describes a method for the extraction of proanthocyanidins from plant material. The method involves heating an aqueous mixture of solid plant material, optionally under increased pressure and reduced oxygen followed by various separation, filtration and adsorption steps, and the elution of adsorbed proanthocyanidins with polar solvent. This method also is amenable to reconstituting and recycling the polar solvent into the elution phase of the method, resulting in decreased solvent consumption and a more cost-effective process.

U.S. Pat. No. 4,211,577 describes the extraction of plant anthocyanin colors by treating impure materials to insure discrete monomeric anthocyanin molecules in solution and then passing the solution through ultrafiltration membranes to retain soluble and/or cloudy macromolecular, e.g., colloidal, impurities upstream that produce, an aging, haze and sediments, and passing the monomeric anthocyanins downstream for further concentration as liquid or powder to give a stable color concentrate that can be used as a color additive. In this manner, fruit solids may be treated with sulfur dioxide solutions to ionize, decolor and insure the monomeric state of the pigment molecules (change from anthocyanins to chromon 2- and 4-sulfonates). Ultrafiltering the solution to pass the anthocyanins downstream while retaining upstream the macromolecular components such as pectins, tannins, proteins, complexes thereof, etc. Optionally stripping of the sulfur dioxide from the ultrafiltered solution regenerates the original anthocyanins from the chromen sulfonates. The anthocyanins can then be concentrated by evaporation to a highly concentrated liquid from which unstable pigments with acyl groups in the molecule may optionally be removed by controlled precipitation at reduced temperatures.

U.S. Pat. No. 4,302,200 describes a process for the extraction of anthocyanins from a natural product by bringing the natural product containing the anthocyanin into contact with a sulfite ion-containing aqueous solution at a temperature of 85° C. or higher for 30 minutes or less, at which time the sulfite ion content of the aqueous solution firstly contacting the natural product is adjusted to at least 10,000 ppm in terms of $SO_2$.

U.S. Pat. No. 3,963,700 describes a method of recovering anthocyanins from plant materials such as grape wastes using a tartaric acid-alkanol extraction followed by controlled precipitation of excess tartaric acid as potassium hydrogen tartrate. This patent further describes the use of these anthocyanins in the preparation of an artificial grape drink colored with the anthocyanin extract.

While it is contemplated that the methods described in the above patents will be useful in generating the anthocyanins for the anti-inflammatory properties described herein, the inventors have developed another method of extraction of anthocyanins from a natural source.

The method is directed to concentrating flavonoids from plants without the use of undesirable chemicals. The process includes passing a solution containing one or more flavonoids through an ultrafiltration membrane to provide a supernatant and a retentate. The supernatant is then passed through a reverse osmosis membrane to provide a retentate and a permeate, and then the reverse osmosis retentate is collected.

The molecular weight cutoff of the ultrafiltration membrane is preferably in the range of about 100,000 to about 1,000,000. The molecular weight cutoff of the reverse osmosis membrane is preferably in the range from about 1,000 to about 10,000.

The collected retentate contains the anti-inflammatory, COX-2 inhibiting properties that are described in the present invention. In preferred embodiments the retentate may thus be dried and combined with one or more excipients to provide a dietary supplement.

Referring now to FIG. 1, there is shown a flow sheet of one embodiment of the process according to the present invention. In accordance with this embodiment, a plant source 1, particularly a fruit containing flavonoids and more particularly a fruit containing anthocyanin compounds is processed by an extraction method 10 to obtain an extract or juice 2. For example, the plant may be subjected to a juicing operation or a pressing operation such as a screw or bag press to obtain a cake and a juice. Alternatively, the raw plant may be ground, pulverized or subjected to process to increase the surface area of the plant to facilitate the extraction and separation of the desired flavonoid compounds from the bulk solids To aid in this separation and to obtain a better ultimate recovery of the desired anthocyanin compounds, it may be desirable to contact the plant with an extractant 3 to obtain an extract juice) rich in flavonoids (particularly the anthocyanin compounds) and to form a bulk solid residue or cake 4. Preferably, the extractant is water in order to minimize further separation processing steps. The extracting step may be done using conventional extraction equipment, in countercurrent fashion, batch, or multiple batch extraction.

In addition, the cake may likewise be subjected to an extraction process to increase the recovery of the desired anthocyanin compounds. If this extraction process step is conducted, it may be desirable to combine the extract from this step with the juice and/or extract (juice) from the previous step.

The juice may separated from the cake in any known manner using bulk separation apparatus such as a centrifuge, screen, press, or filter. Prior to ultrafiltration, the bulk solids are desirably separated from the liquid by any known bulk separation apparatus. For example, the following may be used a centrifuge, filter, screen, press, etc.

Thereafter, an ultrafiltration process 20 is used to remove suspended particles and colloidal high molecular weight components having a molecular weight greater than about 200,000 Daltons. The ultrafiltration membrane can be a tubular type, a capillary type, spiral type, hollow fiber, or other suitable type. The membrane can be polysulphone, polyacrylonitrile, polyethersulphone, PVDF or other suitable material. Preferably, the ultrafiltration is conducted using cross-flow. The molecular weight cut off of the membrane can range from about 20,000 Daltons to about 300,000 Daltons, preferably about 200,000 Daltons. If there is no filtration before the ultrafilter, it is preferred to use a higher molecular weight cut off membrane so that an acceptable filtration rate can be achieved. Thus, it is contemplated to incorporate a microfiltration step before the ultrafiltration step.

For example, a microfilter may be used to remove suspended particles having a size in the range from about 0.01 to about 1 micrometer.

The ultrafiltration can be conducted under a pressure of about 5 to about 25 bar and at a temperature of about 20° C. to about 80° C. This step primarily removes the lipids, proteins and like colloids, cell fragments, starch, etc. with the advantage that the following RO step can be carried out free of the contamination of the membrane(s) that would otherwise lead to a reduced filtration rate.

The ultrafiltration step results in a permeate 5 rich in anthocyanin compounds and a retentate 7 containing undesirable compounds. To increase the ultimate recovery of the flavonoids and desired anthocyanin compounds, a difiltrate 6 may be provided to the ultrafiltration membrane.

The ultrafiltration permeate 5 is subjected to reverse osmosis 30 to provide a retentate 8 rich in flavonoids, including the anthocyanin compounds, and a permeate 10, which is substantially free of the flavonoids, including the anthocyanin compounds. To increase the ultimate recovery of the flavonoids and desired anthocyanin compounds, a difiltrate 9 may be provided to the ultrafiltration membrane. The membrane to be used for the RO of the present invention can be polyethersulphone, polysulphone, cellulose acetate, or a polyamide film.

The reverse osmosis can be conducted at a pressure from about 30 to about 70 bar and at a temperature from about 30° C. to about 80° C., preferably the temperature is maintained in the range from about 30° C. to about 45° C. In general, the reverse osmosis membrane has a molecular weight cutoff in the range from about 1,000 to about 10,000, preferably about 2,000 to provide a retentate.

The retentate contains a higher concentration of the desired anthocyanin compounds than found in the starting plant material. The retentate may be left in the form of a solution but also may be further concentrated by drying 40 to remove some of the water or may be completely dried to form a powder 11.

Where a more concentrated solution is desired, some of the water may be removed by conventional means including use of reverse osmosis membranes having greater than 90% NaCl retention.

Spray drying is the preferred drying means but other drying methods, e.g. flash drying, freeze drying, fluidized bed drying, ring drying, micron drying, tray drying, vacuum drying, radio-frequency drying, or microwave drying, may also be adapted for use in this drying step.

Before drying, it may be desirable to add one or more flow control agents such as maltodextrin (e.g. M100), magnesium hydroxide or other known flow controls agents or carriers. In general, it may be desirable to add a flow control agent in an amount from about 20 to 60% by weight of the solid content in the retentate.

When spray drying is used, the total solids content of the retentate should be at least about 1%, based on the total slurry weight although higher total solids content in the range of at least about 20% to about 35% solids would be desired. The higher solids content levels are desirable since the amount of water that must be removed during the drying step is accordingly reduced. Consequently, the solids content of the retentate will be as high as can be achieved and yet allow efficient processing conditions. The upper limit on solids content in the retentate is typically determined by the operating constraints of the membrane used in the reverse osmosis/nanofiltration step as well as the drying apparatus used.

The temperature of the retentate is not critical. Ambient temperatures, of from about 10–25° C., will generally be preferred. Higher slurry temperatures may be used, and these may be desirable with certain types of drying equipment.

Conventional spray drying equipment may be used, and operating procedures that are familiar to those experienced in the spray drying art are applicable to the spray-drying step of this process. Drier (drier gas) outlet temperature is ordinarily used to control the residual moisture level obtained in the resulting powder. In a spray drying process, drier outlet temperatures are ordinarily in the range of about 40–100° C. In general, it is desirable to maintain the outlet temperature to less than about 80° C. to minimize the potential for degradation of the desired anthocyanin compounds. It is understood that the corresponding drier inlet temperatures are higher, ordinarily in the range of about 90° C. to about 200° C., but preferably less than about 150° C.

The product recovered from the drying operation is a free-flowing particulate solid that typically has a fine granular powder appearance and is suitable for use as a dietary or food supplement. In this regard, the resulting powder containing the desired one or more anthocyanin compounds is useful as a food or dietary supplement.

The reverse osmosis permeate may be further processed by, for example, a concentrator 50 to provide a concentrate 12 that may be used to prepare a fruit drink.

Of course the above is only one method and it should be understood that any method, which provide fruit extracts possessing an anti-inflammatory activity greater than the anti-inflammatory activity found in the natural fruit, will be useful in the context of the present invention.

Although any of the above methods are suitable for obtaining the desired anthocyanin, it is also contemplated that commercially available extracts may be used for some or all of the requirements of the products of the present invention. As an example, it is known that Artemis International of Fort Wayne, Ind. supplies juice concentrates and powders that contain anthocyanins and other flavonoids. Where commercial products are used, it is preferred that the anthocyanin content in the extract is at least 10% by weight of the extract product.

C. Identification of Anthocyanin and Novel Anti-inflammatory Compounds

The present section is directed towards providing a general teaching of the purification and identification of such compound(s).

In general, the plant extract may be prepared as described herein above, obtained from another method, or obtained from a commercial source. The plant extract will comprise a mixture of flavonoid compounds some of which will have COX-2 selective activity, others of which will have COX-1 selective activity, still others which will have a broad spectrum cyclooxygenase inhibitory activity and still others which will not have any appreciable inhibitory activity of cyclooxygenase inhibition.

Upon demonstrating that a particular plant extract has an anti-inflammatory activity, using for example the assays described herein below or other equivalent assays known to those of skill in the art for measuring COX activity, it will be possible to separate the individual components of the fruit extract. Separation techniques are well known to those of skill in the art. For example, those of skill in the art may employ chromatography such as thin layer chromatography, gas chromatography, high performance liquid chromatography, paper chromatography, affinity chromatography, ion exchange chromatography, supercritical flow chromatography and the like to separate the individual flavonoid components (See Freifelder, Physical Biochemistry Applicatons to Biochemistry and Molecular Biology, 2nd ed., Wm. Freeman and Co., New York, N.Y., 1982 for an overview of chromatographic techniques).

Partition chromatography is based on the theory that if two phases are in contact with one another, and if one or both phases constitute a solute, the solute will distribute itself between the two phases. Usually, partition chromatography employs a column that is filled with a sorbent and a solvent. The solution containing the solute is layered on top of the column. The solvent is then passed through the column, continuously, which permits movement of the solute through the column material. The solute can then be collected based on is movement rate. The two most common types of partition chromatograph are paper chromatograph and thin-layer chromatograph (TLC); together these are called adsorption chromatography. In both cases, the matrix contains a bound liquid. Other examples of partition chromatography as gas-liquid and gel chromatography.

Paper chromatography is a variant of partition chromatography that is performed on cellulose columns in the form of a paper sheet. Cellulose contains a large amount of bound water even when extensively dried. Partitioning occurs between the bound water and the developing solvent. Frequently, the solvent used is water. Usually, very small volumes of the solution mixture to be separated is placed at top of the paper and allowed to dry. Capillarity draws the solvent through the paper, dissolves the sample, and moves the components in the direction of flow. Paper chromatograms may be developed for either ascending or descending solvent flow. Two dimensional separations are permitted by changing the axis of migration 90° after the first run.

Thin layer chromatography (TLC) is very commonly used to separate lipids and, therefore, is considered a preferred embodiment of the present invention. TLC has the advantages of paper chromatography, but allows the use of any substance that can be finely divided and formed into a uniform layer. In TLC, the stationary phase is a layer of sorbent spread uniformly over the surface of a glass or plastic plate. The plates are usually made by forming a slurry of sorbent that is poured onto the surface of the gel after creating a well by placing tape at a selected height along the perimeter of the plate. After the sorbent dries, the tape is removed and the plate is treated just as paper in paper chromatography. The sample is applied and the plate is contacted with a solvent. Once the solvent has almost reached the end of the plate, the plate is removed and dried. Spots can then be identified by fluorescence, immunologic identification, counting of radioactivity, or by spraying varying reagents onto the surface to produce a color change.

TLC of anthocyanins from bilberry extracts is described by Petri et al., (1994). This reference also describes additional spectrophotmetric and chromatographic techniques that can be used in the identification and characterization of anthocyanin agents.

In gas liquid chromatography (GLC), the mobile phase is a gas and the stationary phase is a liquid adsorbed either to the inner surface of a tube or column or to a solid support. The liquid usually is applied as a solid dissolved in a volatile solvent such as ether. The sample, which may be any sample that can be volatized, is introduced as a liquid with an inert gas, such as helium, argon or nitrogen, and then heated. This gaseous mixture passes through the tubing. The vaporized compounds continually redistribute themselves between the gaseous mobile phase and the liquid stationary phase, according to their partition coefficients.

The advantage of GLC is in the separation of small molecules. Sensitivity and speed are quite good, with speeds that approach 1000 times that of standard liquid chromatography. By using a non-destructive detector, GLC can be used preparatively to purify grams quantities of material.

Gel chromatography, or molecular sieve chromatography, is a special type of partition chromatography that is based on molecular size. The theory behind gel chromatography is that the column, which is prepared with tiny particles of an inert substance that contain small pores, separates larger molecules from smaller molecules as they pass through or around the pores, depending on their size. As long as the material of which the particles are made does not adsorb the molecules, the sole factor determining rate of flow is the size. Hence, molecules are eluted from the column in decreasing size, so long as the shape is relatively constant. Gel chromatography is unsurpassed for separating molecules of different size because separation is independent of all other factors such as pH, ionic strength, temperature, etc. There also is virtually no adsorption, less zone spreading and the elution volume is related in a simple matter to molecular weight.

The gel material for gel chromatography is a three-dimensional network whose structure is usually random. The gels consist of cross-linked polymers that are generally inert, do not bind or react with the material being analyzed, and are uncharged. The space filled within the gel is filled with liquid and this liquid occupies most of the gel volume. Common gels are dextran, agarose and polyacrylamide; they are used for aqueous solution.

High Performance Liquid Chromatography (HPLC) is characterized by a very rapid separation with extraordinary resolution of peaks. This is achieved by the use of very fine particles and high pressure to maintain an adequate flow rate. Separation can be accomplished in a matter of minutes, or at most an hour. Moreover, only a very small volume of the sample is needed because the particles are so small and close-packed that the void volume is a very small fraction of the bed volume. Also, the concentration of the sample need not be very great because the bands are so narrow that there is very little dilution of the sample. HPLC set up with a photodiode array detection system has been used to study flavonoids such as rutin and other quercetin glycosides, phloridzin, as well as certain anthocyanins (Paganga and Rice-Evans, FEBS Lett. 401(1):78–82, 1997). A reverse phase-HPLC gradient procedure has been described for the separation and quantitative estimation of 12 anthocyanins (Petri et al., Acta Pharm. Hung. 64(4) 117–122, 1994). Quercetin compounds also may be identified using the HPLC techniques described by Laires et al., (Food Chem. Toxicol., 31(12) 989–994, 1993). It is contemplated that such methods may be adapted to the present invention in characterizing and identifying novel flavonoids.

Affinity Chromatography is a chromatographic procedure that relies on the specific affinity between a substance to be isolated and a molecule that it can specifically bind to. This is a receptor-ligand type interaction. The column material is synthesized by covalently coupling one of the binding partners to an insoluble matrix. The column material is then able to specifically adsorb the substance from the solution. Elution occurs by changing the conditions to those in which binding will not occur (alter pH, ionic strength, temperature, etc.).

The matrix should be a substance that itself does not adsorb molecules to any significant extent and that has a broad range of chemical, physical and thermal stability. The ligand should be coupled in such a way as to not affect its binding properties. The ligand should also provide relatively tight binding. And it should be possible to elute the substance without destroying the sample or the ligand. One of the most common forms of affinity chromatography is immunoaffinity chromatography which employs antibodies directed against the particular materials to be detected.

The structure of anthocyanins separated using the above techniques can be identified by generating mass spectra and NMR spectra as described by Saito et al., (Phytochemistry 41(6) 1613–1620, 1996 and Phytochemistry 43(6), 1365–1370, 1996); Takeda et al., (Phytochemistry, 36(3) 613–616,1994). Additional NMR techniques are described by Terahara et al. (BioSci. Biotech. Biochem., 58(7) 1324–1325, 1994); Nerdal et a., (Acta Chem. Scand. 46(9) 872–876,1992). Johansen et al., (Phytochemistry 30(12) 4137–4141, 1991) describe various methods including ion-exchange resin, droplet-counter chromatography and gel filtration for the isolation of anthocyanins and the subsequent use of techniques such as chemical degradation, chromatography and spectroscopy, especially homo- and heteronuclear two-dimensional NMR techniques for the characterization of the isolated anthocyanin compounds. It will be clear to those of skill in the art that any of the above described techniques can be used to isolate and further purify the fruit extracts described herein to identify the individual compounds responsible for the anti-inflammatory activity.

D. Assays to Test for Anti-inflammatory Activity

In the present invention, it is described that anthocyanin-containing plant extracts have an anti-inflammatory activity.

More particularly, it is demonstrated that such extracts inhibit COX-2 activity preferentially over COX-1 activity. As such these extracts provide an excellent alternative to the traditional NSAIDs in that they are selective for COX-2. These inhibitory extracts are further advantageous over the recently developed, COX-2 specific "super aspirins" because these extracts are natural extracts that have not been linked to increased propensity for heart attacks, strokes, and other adverse cardiovascular events.

The concentration of any inhibitor that inhibits the enzyme to 50% of its maximal activity is called $IC_{50}$ or $I_{50}$. The smaller the $IC_{50}$, the stronger or more potent the corresponding inhibitor is for the enzyme inhibition. Consequently, a smaller amount of inhibitor would be required for anti-inflammatory and pain-relief supplement formulation if the compound can be absorbed, metabolized, transported to the malfunctional or diseased site.

Some materials, compounds, or plant concentrates may selectively inhibit either COX-1 or COX-2 enzyme. This can be referred to as selectivity of the material. The selectivity can be numerically expressed by the ratio of $I_{50}$ (COX-1)/$I_{50}$ (COX-2). When the ratio is equal to 1, the inhibitor has no selectivity for either of the isozymes; i.e. the inhibitor is equally inhibiting COX-1 and COX-2 enzymes. When the ratio is less than 1, the inhibitor is more selective for COX-1 inhibition. When the ratio is more than 1, the inhibitor is more selective for COX-2 inhibition. For chronic anti-inflammatory and pain-relief drugs or supplements, the selectivity may play a key role in side effects. The side effects are mostly gastrointestinal (GI) bleeding caused by the inhibition of COX-1 enzyme on the GI tract where prostaglandins have a normal function on GI lining.

The selectivity is an important issue in non-sterol anti-inflammatory drugs (NSAIDs), because NSAIDs only have one active form that can inhibit constitutively expressed COX 1 enzyme in GI tract and cause GI bleeding, in addition to the expected action of absorption and transportation to the inflammatory and pain sites. Though not yet proven, natural products, such as anthocyanin-containing plant extracts, may have an advantage because they have non-active and active forms and therefore, may not cause side effects in GI tract. Different mechanisms of absorption, metabolism and transportation may exist. It is possible that the non-active form (glycosidic form with sugar) can be absorbed or passed through the GI tract without inhibiting the COX-1 enzyme there. As a result, the amount of prostaglandins generated by COX 1 enzyme on the GI tract is normal or high enough to maintain the GI lining. After the absorption, the sugar moiety is cleaved and the active form (aglycone form, anthocyanidin) is transported to the site where COX 2 enzyme is induced at great level, although COX 1 will be inhibited as well (but to a lesser degree). The inhibition of both enzymes on the site will be very effective in anti-inflammation and pain relief.

In certain aspects of the present invention, it will be necessary to determine whether a particular plant extract or a component thereof possesses an anti-inflammatory activity. Such an activity may be measured using anti-inflammatory assays well known to those of skill in the art. The use of prostaglandin endoperoxide synthase-1 and -2 isozymes will allow a facile determination of whether a particular extract has the appropriate activity. These assays determine the ability of these enzymes to convert arachidonic acid to prostaglandins. Alternatively, an immunoassay method as described below may be used.

Reagents such as arachidonic acid and microsomal suspension of the COX-1, and COX-2 enzymes are readily available to those of skill in the art (e.g., from Oxford Biomedical Research, Oxford, Mich., USA).

Accordingly, COX-2 inhibitory activity of a particular extract may be measured using a method including generally the steps of (a) obtaining a COX-2 microsomal composition; (b) admixing the candidate extract with the COX-2 microsomal composition; and (c) determining the ability of the candidate extract to inhibit the COX-2 activity.

COX-2 activity may be measured by obtaining a microsomal membrane preparation of COX-2 e.g., (5–10 mg protein/ml in an appropriate buffer). COX-2 assay is performed at 37° C. by monitoring the rate of $O_2$ uptake as described (DeWitt et al., Am. J. Med. 95(2A) 40S–44S, 1993; Arch. Biochem. Biophys. 306(1) 96–102; 1993). This assay basically measures the conversion of arachidonic acid to prostaglandin endoperoxide-2. Thus, one unit of cyclooxygenase activity represents the oxygenation of 1 nmol of arachidonic acid/minute (DeWitt et al., 1993 supra). Alternatively, the activity of COX-2 may be measured using chromatography by determining the amount of the product of the COX-2 enzyme using e.g., thin layer chromatography, gas chromatography, high performance liquid chromatography and the like. Yet another way to measure the COX-2 activity would be to employ radio-labeling of substrates and monitoring the amount of radio-labeled end-product(s) of the COX-2 reaction. A preferred way to measure the COX activity is an enzyme immunoassay as is described in greater detail in Example 4. Regardless of the method employed one of skill in the art will be able to tabulate the end measurement as a cyclooxygenase activity e.g., $O_2$ used/mg cyclooxygenase/min; mg product/mg cyclooxygenase/min; $\mu$Ci radio-labeled product produced/mg cyclooxygenase/min; $\mu$Ci radio-labeled arachidonate used/mg cyclooxygenase/min.

To identify a fruit extract as being capable of inhibiting COX-2, one would measure or determine the COX-2 activity of the microsomal preparation in the absence of the added candidate extract. One would then add the candidate extract to the preparation and re-determine the activity in the presence of the candidate extract. A candidate extract which reduces the amount of arachidonate oxygenated relative to the arachidonate oxygenation in its absence is indicative of a candidate extract with COX-2 inhibitory capability.

Control experiments can be conducted in which known inhibitors of COX activity e.g., aspirin, ibuprofen, Celebrex™, naproxen and the like may be used. By comparing the results of the fruit extract with that of the COX-2 activity in the presence of these known inhibitors useful, relative activities also may be determined.

A significant decrease in arachidonate oxygenation, e.g., as measured using oxygen consumption with an $O_2$ electrode, chromatography techniques (quantitation of end-product by densitometry or liquid scintillation spectroscopy), are represented by a reduction in COX-2 activity levels of at least about 20%–40%, and most preferably, by decreases of at least about 50%, with higher values, of course, being possible. Chromatography assays that measure arachidonic acid metabolites and COX enzyme assays that measure prostaglandin formation are well known in the art and may be conducted in vitro or in vivo.

Quantitative in vitro testing of the inhibitory properties of the fruit extract is not a requirement of the invention as it is generally envisioned that the fruit extracts that form the nutraceutical agents of the present invention will often be the same compounds that are naturally found in the whole fruits. Of course, it should be understood that the anthocyanin and flavonoid compounds that form the COX-2 inhibitory components of the fruit extracts described herein may further be modified in vivo upon ingestion to produce the anti-inflammatory compounds.

Similarly, in vivo testing is not a necessary requirement. However, one of skill in the art may employ animal models of inflammation to test for the in vivo activity of these compounds. For example, a rodent model having an inflamed area may be used to test the anti-inflammatory effects of the COX-2 inhibitors that have been identified by assays such as those described above. Such an animal model would be employed in an assay which would use, for example, at least two animals having a similar inflammation, one of the animals would be contacted with the candidate anti-inflammatory composition and the other animal would be contacted with a control or placebo composition which contains all the components of the candidate composition with the notable exception that it lacks the anti-inflammatory component. A reduction in inflammation of the animal contacted with the candidate composition as compared to the animal contacted with the control or placebo composition would be indicative of the candidate composition having anti- inflammatory activity.

E. Formulations

The present invention provides a natural food supplement made from extracts wherein the food supplement comprises an anti-inflammatory activity that is greater than the anti-inflammatory activity found in the natural fruit. The present invention provides an extract that can be presented in a powdered, liquid, or solid form. Specific formulations are provided herein below in the Examples, the present section discusses the forms and components of formulations that would be desirable and readily produced given the teachings of the present invention.

The extract is likely a reconstitutable powder composition that, when reconstituted with, for example, water, milk or some other similar liquid will provide a drink, which may be used to provide an anti-inflammatory activity to a subject in need thereof. The powdered composition and drink prepared therefrom are especially useful as an enterally administered component in a program of pain or inflammation management which utilizes a number of carefully designed products in various forms, i.e., in shake, soup, fruit drink, snack bar and other solid forms such as tablets, gel caps, and the like, which can be mixed and matched over a period of pain management to provide more attractive and, therefore, more effective support to a patient, particularly those in extended care situations.

In addition to drinks, the extracts of the present invention may be used in foodstuffs. Such extracts may be combined with any other foodstuff, for example, oils containing the extracts of this invention may be used as cooking oil, frying oil, or salad oil and may be used in any oil-based food, such as margarine, mayonnaise or peanut butter. Grain flour fortified with the compounds of this invention may be used in foodstuffs, such as baked goods, cereals, pastas and soups. Oils containing the extracts and novel anthocyanins extracted therefrom can be emulsified and used in a variety of water-based foodstuffs, such as drinks, including drink mixes as discussed above. Advantageously, such foodstuffs may be included in low fat, low cholesterol or otherwise restricted dietary regimens.

A "nutraceutical" is any functional food that provides an additional benefit other than its nutritional benefit. This category may include nutritional drinks, diet drinks (e.g., Slimfast™, Boost™ and the like) as well as sports herbal and other fortified beverages. The present invention provides nutraceutical compositions that may be used as an anti-inflammatory agent. As such, it can be used to relieve any condition that is mediated by the action of COX-2 including but not limited to, arthritis, headache, allergic rash, inflammatory bowel syndrome, joint pain, chronic fatigue, fibromyalgia and the like.

In addition to the purified extract, the nutraceutical or foodstuff also may contain a variety of other beneficial components including but not limited to essential fatty acids, vitamins and minerals. These components should be well known to those of skill in the art, however, without being bound to any particularly formulations or content the present section provides a brief discussion of components that could form part of the food supplements of the present invention. Additional disclosure describing the contents and production of nutritional supplements may be found in e.g., U.S. Pat. No. 5,902,797; U.S. Pat. No. 5,834,048; U.S. Pat. No. 5,817,350; U.S. Pat. No. 5,792,461; U.S. Pat. No. 5,707,657 and U.S. Pat. No. 5,656,312 (each incorporated herein by reference.) Essential fatty acids such as γ-linolenic acid (ω-3) and linoleic acid (ω-6) may be added to the food supplements of the present invention. Research has shown that in animals other than humans, the ratio of n-3 to n-6 fatty acids is more important even than absolute amounts of the fatty acids. Boudreau M D, et al., "Lack of Dose Response by Dietary n-3 Fatty Acids at a Constant Ratio of n-3 to n-6 Fatty Acids in Suppressing Eicosanoid Biosynthesis from Arachidonic Acid," Am. J. Clin. Nutr. 54:111–117 (1991). Essential fatty acids are involved in cardiovascular health as well as in support of the immune system. An imbalance in these essential fatty acids can lead to poor cholesterol metabolism. Additionally, the immune system function can become impaired, leading to inflammation.

Both calcium and magnesium are involved in bone health, among other functions. One possible effect of an imbalance between calcium and magnesium is an imbalance in bone minerals that can affect bone growth and bone turnover (the breaking down and building-up of bone). Magnesium is equally as important as calcium for bone health and reducing the risk of osteoporosis, which affects men as well as women(Purvis, J. R., "Effect of Oral Magnesium Supplementation Factors on Selected Cardiovascular Risk Factors in Non-Insulin-Dependent Diabetics," Archives of Family Medicine 3:503–508 (1994).

The minerals zinc and copper are both involved in cardiovascular health, and should be provided in a ratio of 5:1 zinc:copper. An imbalance between these two minerals can cause an antagonistic effect of zinc on copper. This effect can interfere with the body's ability to use copper for supporting cardiovascular health. Too much zinc relative to copper can also interfere with the body's ability to manufacture SOD (superoxide dismutase), an important heart-protective enzyme. Also, a proper zinc:copper ratio is required to achieve a proper balance of HDL (high density lipoproteins) to LDL (low density lipoproteins). Zinc intake in the typical American man's diet is only 33 to 75 percent of RDA as such dietary supplements that include zinc are contemplated.

Selenium and iodide also have a ratio at which they function most effectively, which is the ratio of selenium to iodide of about 2:1. These minerals affect thyroid function, and therefore also have the resulting effects on metabolism caused by changes in thyroid function. Imbalanced thyroid function can put undue stress on the body that will result in malabsorption of nutrients from food. This, in turn, can retard growth and development.

Pyridoxine, folate and cobalamin also have a ratio at which they function most effectively in the prevention of vascular disorders. The optimal ratio of pyridoxine (vitamin B6) to folate to cobalamin (vitamin B12) is about 100:4:1, respectively. These vitamins affect cardiovascular function through their abilities to reduce the levels of the potentially toxic amino acid homocysteine. This ratio recognizes the imbalanced and inadequate levels of these vitamins consumed by individuals at risk of heart disease from their diet.

In addition, vitamin C, vitamin B1 (thiamin), and vitamin E also can be provided. Vitamin C requirements are increased in smokers and cigarette smoking is a major contributor to lung cancer. Vitamin B1 plays an essential role in energy transformation. Thiamin diphosphate (TDP) is a coenzyme necessary for the conversion of carbohydrates to energy. Since U.S. men currently consume about 45% of their total calories from carbohydrates, vitamin B1 optimization in the diet is desirable.

Along with vitamin B6, vitamin B12 and folic acid supplementation help modulate blood levels of homocysteine and as such will be useful components in the dietary supplement formulations of the present invention. Vitamin D (calciferol) is essential for formation of the skeleton and for mineral homeostasis. Without vitamin D, the small intestine cannot absorb adequate calcium regardless of how much calcium is available for absorption. Thus, vitamin D is indicated as a component of a nutritional supplement to help build strong bones.

The role of manganese in driving metalloenzyme manganese-superoxide dismutase (Mn-SOD) has been clearly identified, along with a similar role in other metalloenzyme systems (glutamine synthetase, arginase, and pyruvate carboxylase). Numerous enzyme systems have also been shown to undergo manganese activation, even though they are not manganese metalloenzymes. The manganese-SOD connection may be of special clinical importance, since this form of the metalloenzyme appears to be the sole operative form within the cell's mitochondrial membranes, and thus may play a unique role in protection of the mitochondria and assurance of the body's oxidative energy production system. The inclusion of manganese in a dietary supplement would be desirable.

Additional micronutrients that may be included in the supplements include but are not limited to the vitamins such as vitamin A, vitamin C, vitamin E, riboflavin, niacin, niacinamide, pantothenic acid, pyridoxine, cobalamin, biotin, inositol, choline bitartrate, betaine, and vitamin K and minerals such as molybdenum, chromium and potassium.

Stress, exercise, and other conditions create free radicals in the body, which can cause damage to the body's components. To counter the free radicals, the present invention may include the following antioxidants in addition to vitamins C and E discussed above: citrus bioflavonoids, mixed carotenoids, green tea extract, and N-acetylcysteine.

In addition other flavorings and additives well known to those of skill in the art also may be added to the formulations to make them more palatable. For example, formulations may contain ginger, boswellia, fruit flavoring, coloring, preservatives and the like.

When ingested in a solid form, the nutraceutical composition of the invention may additionally contain a solid carrier such as a gelatin or an adjuvant. When administered in liquid form, a liquid carrier such as water, petroleum, oils of animal or plant origin such as peanut oil, mineral oil, soybean oil, or sesame oil, or synthetic oils may be added.

In some formulations, it may be desirable to use the cake that results from the extraction process used to obtain the anthocyanin-containing extract as some or all of the carrier. For example, cherry cake is a by-product of the cherry juice industry. Often these cakes contain beneficial components such as anthocyanins and bioflavonoids and when used as the carrier, should increase the potency of the formulation. The nutraceutical composition of the present invention may also contain stabilizers, preservatives, buffers, antioxidants, or other additives known to those of skill in the art.

In a preferred embodiment, a dietary or nutritional supplement or nutraceutical is provided and contains from about 0.1% to about 99%, preferably from about 30% to about 90% of an anthocyanin-containing extract. In this regard, a single dosage form (i.e., a single tablet, capsule, serving (whether liquid or solid)) contains from about 1 mg. to about 500 mg. of total anthocyanin, preferably from about 5 mg. to about 100 mg., more preferably from about 20 mg. to about 70 mg. of total anthocyanin. In a preferred formulation, a tablet (a single dosage form) is provided that contains about 35 mg. of total anthocyanin. The phrase "total anthocyanin" refers to the total amount of anthocyanin present in the single dosage form.

The extract obtained from an anthocyanin-containing plant is selected from the group consisting of peonidin, cyanidin, pelargonidin, delphinidin, petunnidin, malvidin, kaempferol, hesperidin, gentiodelphin, platyconin, cinerarin, including their glycoside derivatives, and mixtures thereof. In one a preferred embodiment, the anthocyanins are selected from the group consisting of cyanidin, peonidin, malvidin, petunidin, delphinidin, their glycoside derivatives, and mixtures thereof. Avantageously, the nutritional supplement contains the stable anthocyanin, which will be hydrolyzed in vivio to the aglycone form, anthocyanidin, to provide COX inhibition activity.

A preferred nutritional supplement contains a fruit extract, wherein the fruit extract is selected from the group consisting of an extract of elderberry, tart cherry, bilberry, and mixtures thereof. More particularly, the fruit extract comprises an extract of elderberry in an amount from about 2% to about 98% by weight of the fruit extract, an extract of tart cherry in an amount from about 1% to about 49% by weight of the fruit extract, and an extract of bilberry in an amount from about 1% to about 49% by weight of the fruit extract. Preferably, the extract comprises from about 90% to about 98% (more preferably about 96%) of an elderberry extract, from about 1% to about 5% (more preferably about 2%) of a cherry extract (preferably tart cherry), and from about 1% to about 5% (more preferably about 2%) of a bilberry extract. In this preferred nutritional supplement, cyanidin-based anthocyanins comprise at least about 90% by weight of the total anthocyanins present in the elderberry extract. Preferably, cyanidin-based anthocyanins comprise about 95% and more preferably about 96% by weight of the total anthocyanins present in the elderberry extract. In this regard, the cyanidin is present as a mixture of cyanidin-3glucoside, cyanidin-3-sambunigrin, cyanidin-3,5-diglucoside, and cyanidin-3-samb-5-glucoside. Likewise, cyanidin-based anthocyanins comprise at least about 90% by weight of the total anthocyanins present in the tart cherry extract. Preferably, cyanidin-based anthocyanins comprise about 95% and more preferably about 96% by weight of the total anthocyanins present in the tart cherry extract. In contrast to the elderberry, the cyanidin is present as a mixture of cyanidin-3-glucosyl rutinoside, cyanidin-3-rutinoside, cyanidin-3-glucose, cyanidin-3-rutinoside-haxose, cyanidin-3-rutinoside-pentose, and cyanidin-3-rutinoside.

Finally, the bilberry contains a mixture of malvidin, peonidin, cyanidin, petunidin, and delephinidin based anthocyanins. Each of these anthocyanins comprise about 95% and more preferably about 96% by weight of the total anthocyanins present in the bilberry extract. More particularly, the malvidin is present as malvidin-3-arabinoside, malvidin-3-glucoside, malvidin-3-galactoside. The peonidin is present as peonidin-3-lucoside, peonidin-3galactoside. The cyanidin, petunidin, and delphinidin are present as the 3-glucoside and 3-galactoside.

F. Combinations of Anthocyanins with Other Anti-inflammatory Agents

The present invention in certain aspects describes the beneficial intake of a food supplement having anti-inflammatory properties wherein the food supplement comprises an extract having an anti-inflammatory activity greater than the anti-inflammatory activity found in the natural fruit. Those of skill in the art should understand that such a food supplement may advantageously be combined with other anti-inflammatory agents. Such additional anti-inflammatory agents will, of course, be secondary to the extracts of the present invention and may be any commonly recognized anti-inflammatory agent or indeed may be one that is identified by using the assay presented herein above.

Regardless of whether the additional anti-inflammatory agent is a known anti-inflammatory or is identified using the present invention, the present invention will contemplate the use of various combinations that may be employed. Thus, where the fruit extract is "A" and the other anti-inflammatory agent is "B" the combinations may be as follows:

| | | | | | | | |
|---|---|---|---|---|---|---|---|
| A/B/A | B/A/B | B/B/A | A/A/B | A/B/B | B/A/A | A/B/B/B | B/A/B/B |
| B/B/B/A | B/B/A/B | A/A/B/B | A/B/A/B | A/B/B/A | B/B/A/A | | |
| B/A/B/A | B/A/A/B | A/A/A/B | B/A/A/A | A/B/A/A | A/A/B/A | | |

The extract and the additional anti-inflammatory agent may be contacted with or exposed to a cell either in vivo or in vitro to inhibit the COX-2 activity of the cell. The terms "contacted" and "exposed," when applied to a cell are used herein to describe the process by which an extract and a second anti-inflammatory agent are delivered to a target cell or are placed in direct juxtaposition with the target cell. To achieve a beneficial effect, both agents may be delivered to a cell in a combined amount effective to inhibit COX-2 activity, decrease inflammation, and decrease the production of the inflammation causing prostaglandins or other such effect that will decrease the inflammatory response in a cell or an individual subject in which the cell is located.

Anti-inflammatory agents are well known to those of skill in the art and include agents such as salicylic acid derivatives (e.g. aspirin) paraminophenol derivatives (e.g. acetaminaphen) indole and indene acetic acids (indomethacin, sulindac and etodalac) heteroaryl acetic acids (tolmetin diclofenac and ketorolac, aryl propionic acid derivatives (ibuprofen, naproxen, keopren, fenopren, oxaprozine), anthranilic acids (mefenamic acid, meclofenamic acid) enolic acids (piroxicam, tenoxicam, phenylbutazone and oxyphenthatrazone). These and other anti-inflammatory agents are well known to those of skill in the art and no additional description of these agents need be provided.

G. Combinations with Other Active Therapeutic Agents

According to another embodiment of the present invention, the anthocyanins and/or novel compounds derived from natural sources may be combined with other therapeutic agents. It is contemplated that such combinations may, in some cases, provide synergistic effects.

It is intended that the anthocyanins and/or novel compounds can be combined with any suitable therapeutic agents. In a preferred embodiment, however, a nutritional supplement is provided that contains natural active ingredients. As a result, the preferred active agents are those obtained or derived from natural sources and can include various suitable extracts, for example herbal extracts. The PDR® for Herbal Medicines, the entire contents of which is incorporated herein by reference, provides a suitable listing of the types of herbal and/or plant extracts that may be suitable for combining with the anthocyanins of the present invention.

In one embodiment, a joint health agent is provided with one or more anthocyanin-containing extract for use in improving the joint health in a mammal. In this embodiment, the joint health agent is selected from the group consisting of glucosamine, chondroitan, ginger, boswellia, tumeric, curcumin, fever few, bromelain, and salts, derivatives, and mixtures thereof. In yet another embodiment, a dietary supplement includes at least one prostate health agent that is effective to maintain or improve normal prostrate function with an effective amount of an anthocyanin-enriched plant extract having an anti-inflammatory activity greater than the anti-inflammatory activity found in the plant. In this embodiment, the prostrate health agent is selected from the group consisting of saw palmetto, pumpkin seed, nettle root, and salts, derivatives and mixtures thereof. Another embodiment includes at least one gamma-linolenic acid (GLA) agent that is effective to maintain or improve a woman's general well being during her menstrual cycle in combination with an effective amount of an anthocyanin-enriched plant extract. In this embodiment, the GLA agent is obtained from a source selected from the group consisting of evening primrose, borage, black currant, chasteberry, ginger, and salts, derivatives, and mixtures thereof.

H. Methods of Use of the Novel Formulations

The formulations described above may be used to prevent, reduce, or eliminate the symptoms and conditions associated with pain and inflammation. In addition, these formulations when used to treat inflammation and pain are desirable because they have minimal gastrointestinal side effects. These formulations may also be used in an anti-oxidant capacity to reduce or inhibit the oxidation of a material that results from the exposure to free radicals. Furthermore, these formulations may include the use of anthocyanins with other therapeutic agents that are useful to provide a synergistic result that does not occur with the therapeutic agents alone.

Pain is often defined as the sensory and emotional experience associated with actual or potential tissue damage. Pain can be influenced by physical, mental, biochemical, physiological, social, cultural and emotional factors. Pain is typically categorized as two types; acute or chronic. Acute pain is usually characterized by relatively short, sharp pain. When acute pain persists beyond the expected time required for healing, it is considered chronic pain. (C. Thomas, ed., Taber's *Cyclopedic Medical Dictionary*, F. A. Davis Company, 1993).

Pain is perceived when the nerves that receive and transmit painful stimuli, nociceptors, are stimulated. Nociceptors are located in skin, bones, joints, muscles, and internal organs. The various types of nociceptors sense sharp blows, heat, pressure, temperature, chemical changes or inflammation. They transmit the pain signal to other nerves that send messages to the spinal cord and brain. (Cashman J. N., *The mechanisms of action of NSAIDs in analgesia, Drugs*, 1996; 52:13–23.)

The mechanism of pain first involves the stimulation of the nociceptors. When the nociceptrors are stimulated, the release of substance P, a neuropeptide that modulates cellular responses and increases the pain message, is increased. Substance P can stimulate the release of bradykinin, a neuropeptide that propagates slow pain. Histamine is also released, which evokes pain. Prostaglandins are released by damaged tissue during an inflammation response. Prostaglandin E series (PGEs), prostaglandin $I_2(PGI_2)$, and leukotriene $B_4(LTB_4)$ amplify pain by increasing the sensitivity of the nociceptors to the effects of other mediators or mechanical stimuli. This is called hyperalgesia. (Gilman A, Rail T, Nies A, Taylor P eds, *Goodman and Gilman's The Pharmacological Basis of Therapeutics*, NewYork, Pergamon Press, 1990.

The mechanism of inflammation typically involves 4 main symptoms: redness, warmth, edema (swelling), and pain. When tissue is damaged by mechanical, chemical, biological, or invading organisms, the first thing to happen is that mast cells release histamine. The histamine stimulates dilation of the blood vessels. The increase in blood volume to the area causes redness and the sensation of warmth. Kinins are released, which potentiate the vasodilation. The vasodilation causes plasma that contains mediators of acute inflammation (complement, C-reactive protein, antibodies, neutrophils, eosinophils, basophils, monocytes, and lymphocytes) to leak into the surrounding tissue. This causes the tissue to look swollen. The loss of plasma from the blood causes blood to become more viscous. The blood platelets and leukocytes start to stick together and clump. Platelet aggregation causes the platelets to release serotonin, which participates in the formation of pain. The damaged tissue and cell membranes cause an influx of calcium into the cells, which activates the enzyme phospholipase $A_2$. Phospholipase $A_2$ acts on the phospholipids to release arachidonic acid and produce the pro-inflammatory agent called platelet-activating factor. Neutrophils containing lipoxygenase create chemotactic compounds from arachidonic acid. This provokes the release of cytokinins that potently activate inducible cyclo-oxygenase 2 (COX-2) and inducible nitric oxide synthase (NOS). (Gilman A, Rail T, Nies A, Taylor P eds, *Goodman and Gilman's The Pharmacological Basis of Therapeutics*, New York, Pergamon Press, 1990. Robak J, Gryglewski R J, Bioactivity of flavonoids, Pol J Pharmacol, 1996, 48:555–564.

The enzyme cyclo-oxygenase (COX) acts on arachidonic acid to generate prostaglandin (PG) $G_2$, and $PGH_2$. $PGG_2$ and $PGH_2$ are not stable and are converted into prostacyclin ($PGI_2$) by $PGI_2$synthase, thromboxane ($TXA_2$) by $TXA_2$ synthase, and stable prostaglandins $PGD_2$, $PGE_2$, $PGF_2'$. NOS forms nitric oxide and free radicals. Free radicals increase membrane permeability and provide a chemotactic signal for specialized cells, is, neutrophil polynuclears, macrophages, and lymphocytes. Also, the enzyme lipoxygenase can act on arachidonic acid to generate leukotrienes from 5-HETE. The end result is inflammation and pain. (Cashman J. N., *The mechanisms of action of NSAIDs in analgesia*, Drugs, 1996; 52:13–23; Robak J, Gryglewski R J, Bioactivity of flavonoids, Pol J Pharmacol, 1996, 48:555–564).

Pain can be caused by a variety of conditions, and certain classes of drugs that relieve pain are unsuitable for specific types of pain. Therefore, determining the cause of the pain is important in determining the most effective treatment. For example, neuropathic pain caused by nerve damage, or complex regional pain syndromes are effectively treated with antidepressants, anticonvulsants, or α2-agonists, but not opioids (i.e. morphine). Crampy intestinal or constipation-induced pains are best treated with antispasmodic drugs; opioids are not effective. Opioids are most effective at treating acute pain syndromes. Arthritis can be treated with nonsteriodal anti-inflammatory drugs (NSAIDs), whereas peptic ulcer pain is not helped with NSAIDs. Finally, psychological, such as 'phantom pain' or spiritual pain can not be treated with analgesics. (Wilder-Smith CH, Pain treatment in multmorbid patients, the older population and other high-risk groups. The clinical challenge of reducing toxicity, Drug Saf., 1998, 18:457–472.).

Currently, there are five main categories of drugs available to treat pain. These include 1) analgesics (e.g. acetaminophen), 2) salicylates (e.g. aspirin) and other NSAIDs (e.g. ibuprofen and naproxen), 3) opoid drugs (e.g. codeine and morphine), 4) corticosteroids, and 5) adjuvant agents (e.g. antidepressants, anticonvulsants) (Aronson, M. D., Nonsteroidal anti-inflammatory drugs, traditional opoids, and tramadol; *Clin Ther.* 1997; 19:420–432. (Aronson M D, Nonsteroidal anti-inflammatory drugs, traditional opioids, and tramadol: contrasting therapies for the treatment of chronic pain, *Clin Ther.*, 1997,19:420–432, discussion 367–428.).

The formulations described herein include at least one anthocyanin-containing compound from a natural source that may be used to alleviate or reduce pain in a mammal. In one embodiment of the invention, the compound is an extract obtained from an anthocyanin-containing plant selected from the group consisting of sweet cherry, tart (sour) cherry, acerola cherry, plum, bilberry, blackberry, black currant, red current, chokeberry, blueberry, strawberry, cranberry, boysenberry, grapes, red raspberry, black raspberry, elderberry, loganberry, barberry, pomegranate, red cabbage, blue and purple potatoes, purple carrot, black beans, black soybeans, hibiscus, echinacea purpea, and mixtures thereof. A preferred group of anthocyanin-containing plants include strawberry, acerloca cherry, plum, cranberry, grapes, pomegranate, red cabbage, blue and purple potatoes, purple carrot, and echinacea purpea. A more preferred group of anthocyanin-containing plants include sweet cherries, blueberries, red rasberry, blackberry, loganberry, black beans, black soybeans, hibiscous, and barberry. The most preferred anthocyanin-containing plants include elderberry, chokeberry, tart cherry, bilberry, black raspberries, and boysenberry. In another embodiment, elderberry is preferred as the natural source of the anthocyanin-containing compound.

The extract from the anthocyanin-containing plant is provided in an amount that is effective to alleviate or reduce pain. The extract is typically included in a unit dosage form. In general, the extract comprises at least about 1% by weight of the unit dosage form. Depending on the extract used and the diluent or excipient that is appropriate for that extract, the extract may comprise up to about 99% by weight of the unit dosage form. Generally, an extract containing at least about 4% by weight of anthocyanins will be effective to alleviate or reduce pain. In another embodiment, an extract that is substantially free of anthocyanidins will be effective to reduce or alleviate pain. As used herein, "substantially free" means that the extract does not contain anthocyanidins that are formed when anthocyanins are hydrolyzed. However, an extract that is substantially free of anthocyanidins may include small amounts of anthocyanidins that normally occur in the natural source or small amounts that are formed by a concentrating process, excluding any hydrolyzation processes.

The anthocyanin-containing extract can be used to alleviate or reduce acute pain or chronic pain. In yet another embodiment, the anthocyanin-containing extract is used to alleviate or reduce one of more symptoms of pain. Pain symptoms that may be alleviated or reduced include, but are not limited to, headache, joint pain, muscular pain, dysmenorrhea, inflammation, and combinations thereof. Formulations that include an effective amount of an anthocyanin-containing extract are well suited for treating or controlling inflammation related diseases such as arthritis and gout. These anthocyanin-containing extracts can be used for inhibiting the cyclooxygenase or prostaglandin H synthase enzymes. In one particular embodiment, the cyclooxygenase or prostaglandin H synthase enzymes are inhibited by providing an anthocyanin selected from the group consisting of cyanidin-3-glucoside, cyanidin-3,5-glucoside, cyanidin-3-sambubioside, cyanidin-3-sambubioside-5-glucoside, and mixtures thereof isolated from the fruit of elderberry to inhibit the enzymes.

When dual inhibitor NSAIDs (NSAIDs that inhibit both the COX-1 and COX-2 enzymes) are used long-term to relieve pain and/or inflammation, the risk of developing gastrointestinal complications is moderate to high. Examples of gastrointestinal complications include ulcers, perforation of the stomach or intestines, gastric outlet obtruction and bleeding. In contrast, formulations that include an anthocyanin-containing extract can be used to reduce or alleviate pain and/or inflammation with minimal gastrointestinal side effects. In one embodiment, a method of alleviating or reducing pain or its symptoms in a mammal is provided wherein the method does not produce significant erosions in the gastric lining. In another embodiment, the method does not exhibit a significant propensity to induce gastric or intestinal ulceration.

I. EXAMPLES

The following examples are included to demonstrate a preferred embodiment of the invention. However, those of skill in the art should, in light of the present disclosure, appreciate that many changes can be made in the specific embodiment disclosed and still obtain a like or similar result without departing from the spirit and scope of the invention.

Example 1

100 kilograms of cherries were pressed using a bag press and the juice was collected. The collected juice was filtered at a temperature less than about 38° C. through an ultrafiltration unit having a 200,000 molecular weight cutoff. The UF unit was operated so that the retentate contained less than 0.5% by weight solids.

Thereafter, the permeate from the UF unit was subjected to reverse osmosis using a membranes having a 4,000 molecular weight cut off. The reverse osmosis step continues until the retentate contains about 1% or less by weight solids.

The retentate is collected in a tank and concentrated to at least 20% by weight solids by a vacuum evaporator at a temperature of less than about 52° C. to avoid degradation of the concentrated flavonoids.

The concentrate is combined with maltodextrin and spray dried with the outlet temperature of the spray drier maintained at a temperature less than about 27° C.

The retained pulp from the bag press was collected, dried, and milled.

Example 2

A batch consisting of 38.8 kilograms of tart cherries was pressed in a bag press to produce 19.3 kilograms of juice and 18.6 kilograms of cake. The juice, which had a pH of 3.3 was pumped to an ultrafiltration membrane at a flow rate between 1770 and 1950 g/min, a pressure of 10 bar, and a temperature ranging from initial 29° C. at the start of the filtration to 18° F. at the end of the filtration. A difiltrate flow was initiated and continued until the dissolved solids in the permeate were about 0.2% by weight.

The ultrafiltration membrane was a PVDF polymeric membrane having a rated 100,000 molecular weight (Daltons) cut off. A suitable membrane can be obtained from PCI Membrane Systems under the tradename FP.

At the end of the ultrafiltration, 53.7 kilograms of permeate containing 5% by weight solids and 3.49 kilograms of retentate containing 0.3% by weight solids was collected. The permeate was then subjected to nanofiltration/reverse osmosis at a feed pressure of 40 bar and a flow rate ranging initially from 1290 g/min to finally 1380 g/min at temperature of 24° C. at the start of the process and a temperature of 41° F. at the completion of the process. A difiltrate of 72.4 kilograms of water was used.

A polyethersulphone membrane having a 4,000 molecular weight (Daltons) cut off was used. A suitable membrane can be obtained from PCI Membrane Systems under the tradename ES404.

Upon completion of this step, 6.4 kilograms of retentate was collected and it contained 1% by weight solids. 117 kilograms of permeate containing 2% by weight solids was recovered.

To produce a powder, the retentate was combined and mixed with 79 grams of maltodextrin M100 and the resulting product was introduced into a spray drier with an inlet temperature of about 140° C. and an outlet temperature of about 90° C. to produce about 105 grams of powder.

Example 3

Comparison of COX-2 and COX-1 Inhibitory Activity of Fruit Extracts

The present example describes an enzyme assay method using an oxygen monitoring system to monitor the COX inhibitory activity of fruit extracts. In this assay the changes of concentration of dissolved oxygen are constantly monitored by an oxygen electrode in a Dissolved Oxygen Measuring System (Instech, Plymouth Meeting, Pa). The output is recorded by a linear Recorder (Fisher Scientific, Pittsburgh, Pa.).

Each day a fresh potassium chloride solution (15 g/100 ml distilled water) was made and the electrode was set up according to manufacturers instructions. The chamber is kept at 37° C.

A prostaglandin assay kit was used and the assay set up in a manner similar to that described for the COX-1 assay. Briefly, 50 µl phenol was added to 20 ml 100 mM Tris buffer, warmed to 37° C. for 1 minute (working buffer). To a tube of hematin 0.9 ml of the working buffer was added. 50 µl 0.1 NaOH was added to an arachidonic acid vial and vortexed. 0.43 ml water was added and the solution mixed again. Samples of extracts were weighed and dissolved in the working buffer to a final concentration of 0.1 g/ml. Buffer, samples or diluted samples are used in the enzyme assays directly.

The enzyme assay is performed according to the manufacturer's instruction, which should be well known to those of skill in the art. Briefly, 600 µl of working buffer were drawn into the chamber from the overflow outlet with the injection valve close, and the main outlet connected to a syringe in the right orientation. The stir bar was set a speed of 3 k/min. At 1 minute intervals, 5 ul enzyme, 15 ul hematin solution, 6 ul buffer or sample or diluted sample and 8 ul arachidonic acid solution was injected. The oxygen concentration changes were transformed into mV and recorded. When the arachidonic acid was added, the consumption of oxygen or the decrease of oxygen concentration was apparent.

There were clear trends in selectivity among the samples tested as indicated by the tables given below.

TABLE 3

COX-1 and COX-2 IC50 values and Specific Activity

| Sample | COX-1 IC50 | COX-2 IC50 | Specific Activity* |
|---|---|---|---|
| Aspirin | 1/20,000 | 1/10,000 | 0.5 |
| Montmorency Tart Cherry Primer | 1/20,000 | Not available | NA |
| Balaton Tart Cherry Prime | 1/5,000 | 1/23,000 | 4.6 |
| Milne Tart cherry | 1/2,500 | Not available | NA |
| Artemis Blueberry | >>1/1,000 | 1/10,000 | NA |
| Artemis Chokeberry | 1/2,000 | 1/15,000 | 7.5 |
| Artemis Elderberry | 1/3,000 | 1/23,000 | 10.1 |
| Nutrilite Acerola Cherry | 1/20,000 | Not available | NA |
| Celebrex | 1/4,000 | 1/28,000 | 7 |
| Quercetin standard | 1/3,500 | 1/22,000 | 6.3 |
| Artemis Bilberry | 1/12,000 | 1/15,000 | 1.25 |

*The higher this number the more selective the extract is for COX-2 as opposed to COX-1.

In addition the COX-2 potency was monitored in relation to Celebrex, a well known COX-2 specific inhibitor.

TABLE 4

COX-2 Potency in relative to Celebrex
The method described above was used to determine the COX-2 inhibition of various inhibitor candidates and compared to Celebrex, a known COX-2 inhibitor.

| Sample | COX-2 | Potency compared to Celebrex |
|---|---|---|
| Artemis Chokeberry | 1/15,000 | 54% |
| Artemis Elderberry | 1/23,000 | 82% |
| Artemis Blueberry | 1/10,000 | 36% |
| Balaton Tart Cherry Prime | 1/23,000 | 82% |
| Quercetin Standard | 1/22,000 | 75% |
| Celebrex | 1/28,000 | 100% |

The data clearly shows the selectivity of the Artemis dark berry samples towards COX-2.

Example 4

A presently preferred method of determining whether an inhibitor candidate inhibits either COX-1 or COX-2 is described below. In general, for each inhibitor candidate, six different concentrations are used for both COX 1 and COX 2 enzyme reactions. The content of PG-2α from standards, or enzyme reactions are quantitated by an immunoassay. The amount of PG-f2α in standards is used to make a standard curve (optical density vs. concentration) and the standard curve is used to calculate the amount of PG-2α in each enzyme reaction (regression) for the samples. Then, the content of PG-2α from the six different reaction concentrations of the same inhibitor candidate is used to make a sample curve. Finally, the concentration of the inhibitor candidate that inhibits the enzyme to 50% of its maximal activity (with no inhibitors), or $I_{50}$ is obtained from the sample curve. To keep the results consistent, one inhibitor candidate or drug is used for each set of experiments as a positive control.

COX-1 and COX-2 enzymes were obtained from Dr. Daniel Tai at the University of Kentucky. They were prepared as follows: COX-1 enzyme was extracted from human platelet concentrate obtained from the Central Kentucky Blood Center. The platelet suspension was centrifuged at 1,000 xg for 10 min. The pellet was washed with the same volume of phosphate-buffer saline and the suspension was again centrifuged. The platelets were suspended in 5 volumes of 50 mM Tris-HCl buffer, pH 7.5, and subjected to sonication for 3×20 sec at 4° C. The suspension was centrifuged at 5,000 xg for 10 min. The supernatant was further centrifuged at 100,000 xg for 60 min. The pellet (microsomes) was suspended in 5 ml of 50 mM Tris-HCl buffer, pH 7.5 and stored in 200 μl aliquots at −80° C. This fraction was used as a source of COX-1 enzyme.

Recombinant human COX-2 enzyme was obtained from insect cells (Sf9) infected with recombinant baculovirus carrying COX-2 cDNA. Briefly, Sf9 cells ($1\times10^7$) were seeded in 75 cm² tissue culture flask in 20 ml of complete TNF-FH medium. Cells were allowed to attach for 1 hour. The medium was removed; 4 ml of Grace's medium containing recombinant virus at a multiplicity of about 10 was added. The cells were allowed to grow continuously for 72 hours. Cells were collected by centrifugation at 500 xg for 10 min. The cells were then suspended in 1 ml of 50 mM Tris-HCl, pH 7.5 buffer and sonicated for 3×10 sec at 0° C. The homogenate was briefly spun at 5,000 xg for 5 sec to remove cell debris. The supernatant was then stored in 200 μl aliquots at −80° C. This fraction was used as a source of COX-2 enzyme.

The following buffers were prepared:
1. Coating Buffer: 0.1M $NaHCO_3/Na_2CO_3$, pH 9.5
2. enzyme immunoassay ("EIA") Buffer: 0.1M $KH_2PO_4/K_2HPO_4$, pH7.5 containing 0.9% NaCl and 0.1% bovine serum albumin (ELISA or RIA grade)
3. Antibody Stabilizing Buffer: EIA buffer plus sucrose (5 g per 100 ml) 4. Washing Buffer: 0.01M $KH_2PO_4/K_2HPO_4$, pH7.5 containing 0.05% Tween 20
5. Enzyme reaction buffer and sample dilution buffer: 50 mM Tris-HCl, pH 7.5
6. PBS (phosphate buffer saline) 10 mM $KH_2PO_4/K_2HPO_4$, pH7.5 containing 0.9% NaCl
7. Protein A solution 1 mg/ml in PBS The wells for the immunoassay were coated by (a) adding 100 μl protein A solution to 19.9 ml coating buffer, mixing well, and pouring into a dispensing tray; (b) pipetting 200 μl of the above to each well (rinse many times before delivering to wells); (c) storing the plates at room temperature for 4–5 h or 37° C. for 2–3 h or 4° C. overnight; (d) pipetting 100 μl EIA buffer to each well to block the unfilled sites, shaking and incubating at room temperature for 2 h or at 4° C. overnight. The plates can be stored at 4° C. for an indefinite time if the wells are supplied with water.

| | |
|---|---|
| 1. Arachidonic acid: | 1 mg/ml in ethanol |
| 2. Isoproterenol: immediately before use | 2.5 mg/ml, prepare |
| 3. Hemoglobin: immediately before use | 3.2 mg/ml, prepare |
| 4. $SnCl_2$ | 50 mg/ml in ethanol |
| 5. HCl | 1N |
| 6. K-blue substrate buffer: | Neogen, Lexington, KY |

-continued

| | | |
|---|---|---|
| 7. COX-1 enzyme (as described above): assay | 30 times dilution, use 5 μl per | |
| 8. COX-2 enzyme (as described above) assay | 5 times dilution, use 5 μl per | |
| 9. PGF-2α-antibody (Dr. Tai) well | 5,000X dilution, use 50 μl per | |
| 10. PGF-2α-HRP (Dr. Tai) well | 2,000X dilution, use 100 μl per | |

The following PGF-2α standards were prepared:
A. 1 μg/ml
B. 20 μl A (1 μg/ml) plus 980 μl EIA buffer 1,000 pg/50 μl
C. 200 )μl B plus 1.8 ml EIA buffer 100 pg/50 μl
D. 200 ||l C plus 1.8 ml EIA buffer 10 pg/50 μl

TABLE 5

| Standard (pg/50 μl/well) | B | C | D | Buffer (ml) |
|---|---|---|---|---|
| 0 | | | | 1.0 |
| 5 | | | 0.5 | 0.5 |
| 10 | | | 1.0 | |
| 20 | | 0.2 | | 0.8 |
| 50 | | 0.5 | | 0.5 |
| 100 | | 1.0 | | |
| 200 | 0.2 | | | 0.8 |
| 500 | 0.5 | | | 0.5 |
| 1000 | 1.0 | | | |

Where the inhibitor candidates were extracts of anthocyanin-containing plants, the anthocyanins were extracted, concentrated, and hydrolyzed to provide the aglycone form, e.g., the anthocyanidin. Similarly, where the inhibitor candidates were commercial extracts, the extracts were hydrolyzed to provide the aglycone form. In each case, it was the aglycone form of the anthocyanins that were tested. The hydrolyzed anthocyanins were then dissolved in 0.1% HCl in methanol for testing.

PGF-2α is a prostaglandin and an enzyme reaction is conducted to determine whether the inhibitor candidate effectively inhibits either COX-1 or COX-2 (depending on the enzyme being used). PGF-2α is the indirect stable prostaglandin reduced from the prostaglandin products formed by the enzyme reaction.

The enzyme reaction procedure was conducted as follows: (a) 385 μl of a buffer (50 mM Tris-HCl, pH 7.5) was prepared and mixed at room temperature with 50 μl of isoproterenol, 10μl of hemoglobin, 5 μl of $SnCl_2$, and 5 μl of enzyme (depending on the enzyme to be tested, e.g. COX-1 or COX-2 described above); (b) 455 μl of the mixture (a) was added to tubes that contained 40 μl of the inhibitor candidate, mix; (c) add 5 μl of the arachidonic acid solution to each tube, mix, and incubate at 37° C. for 5 min.; (d) stop the reaction by adding 30 μl of the 1N HCl and mixing; (e) neutralize by adding 30 μl of 1 M Tris-base.

The enzyme immunoassay procedure is a method to measure the amount of PGF-2α generated by the enzyme reaction. The enzyme immunoassay was conducted in the following manner: (a) shake out all the liquid in the well and blot on the paper towel; (b) wash w/200 μl washing buffer 2 times, shake and blot; (c) add 50 μl of the PGF-2α-antibody; (d) add 50 μl STD (PGF-2α) or the enzyme reaction product from above (diluted 50× with EIA buffer); (e) add 100 μl PGF-2α-HRP (in EIA buffer); (f shake and allow the plate to stay at room temperature for 1 hour; (g) wash wells three times by repeating step (b); (h) add 100 μl substrate buffer to each well; (i) incubate at room temperature for 3 to 30 minutes depending on the color development; (j) turn on the computer and 96-well bioassay reader, and follow the operation instructions (Molecular Devices, $V_{max}$ kinetic microplate reader); (k) add 30 μl 1 N HCl to terminate the reaction, (l) read at 420 nm.; (m) save the data.

The data is analyzed by: (a) copying the data to a spreadsheet, (b) making a standard curve according to the standard PGF-2α immunoassay results; (c) finding the PGF-2α amount in all sample enzyme reactions using regression from the standard curve; (d) drawing a curve for each sample; and (e) determining $I_{50}$. In accordance with this procedure, several inhibitor candidates were evaluated and the results in set forth in Table 6, below.

TABLE 6

| Samples | Sample Weight (g) | Final Vol. After purification (ml) | Concentration of total anthocyanidins (mg/ml) | Concentration of cyanidin (mg/ml) | Cyanidin (%) | COX Inhibition (hydrolized liquid samples) | | |
|---|---|---|---|---|---|---|---|---|
| | | | | | | $I_{50}$ (COX 1) (μg) | $I_{50}$ (COX 2) (μg) | $I_{50}$ (COX 1)/ $I_{50}$ (COX 2) |
| A | 1.33 | 2.1 | 1.53 | 0.93 | 61 | 13.2 | 10.7 | 1.2 |
| B | 0.15 | 2.0 | 1.68 | 0.74 | 44 | 19.2 | 21.4 | 0.9 |
| C | 0.15 | 2.0 | 2.92 | 1.36 | 47 | 8.7 | 8.7 | 1.0 |
| D | 0.2028 | 1.0 | 0.20 | 0.20 | 100 | 34.4 | 17.5 | 2.0 |
| E | 0.15213 | 1.0 | 0.17 | 0.17 | 100 | 31.5 | 15.8 | 2.0 |
| F | 0.30784 | 1.0 | 0.057 | 0.046 | 80 | 32.8 | 23.5 | 1.4 |
| Aspirin | | | | | | 100 | 100 | 1 |
| Ibuprofen | | | | | | 8 | 2 | 4 |
| Celebrex | | | | | | 7 | 1 | 7 |
| Vioxx | | | | | | 10 | 0.5 | 20 |

A is a tablet that contains 40% bilberry with 7% anthocyanin
B is a commercial extract from Nutritech containing 25% bilberry
C is a commercial extract from Nutritech containing 25% bilberry from a production lot different from sample B
D is a tablet that contains 39.17% of elderberry that has 15% anthocyanins.
E is a tablet that contains 39.17% of elderberry that has 20% anthocyanins.
F is a tablet that contains 11.76% of elderberry having 15% anthocyanins and 19% bilberry having 7.2% anthocyanins.
Elderberry has 98% cyanidin and its glycosides. Bilberry has 23% cyanidin and its glycosides.

From the above, it appears that the higher cyanidin content increases the potency and selectivity.

Example 5

In accordance with the procedure described in Example 4 above, a number of inhibitor candidates were evaluated. Table 7 presents the results.

TABLE 7

| Extract | $I_{50}$ COX-1 | $I_{50}$ COX-2 | Select-ivity | Content actives |
|---|---|---|---|---|
| Bilberry (from Artemis)* | 29 | 22 | 1.3 | 10.0% |
| Rubini (from Artemis) | 75 | 57 | 1.2 | 7.2% |
| Elderberry proto. | 18 | 14 | 1.3 | 21.0% |
| Bilberry (from Iprona) | 41 | 34 | 1.2 | 2.3% |
| Chockberry (from Iprona) | 117 | 97 | 1.2 | 13.6% |
| Elderberry (from Iprona) | 47 | 35 | 1.3 | 17.0% |
| Bilberry (from Nutratech)* | 14 | 10 | 1.4 | 10.6% |
| Tart Cherry 01-01a* | 250 | 200 | 1.3 | 3.48% |
| Elderberry 004-03* (23% CRR) | 25 | 19 | 1.3 | 15.06% |
| Elderberry 004-04* (0% CRR) | 18 | 14 | 1.3 | 20.15% |
| Pomegranate extract powder | 120 | 80 | 1.5 | n/a |
| Tumeric Extract | 250 | 150 | 1.7 | |
| Boswellia Serrata | 200 | 150 | 1.3 | |
| Panax gotogingseng | 200 | 250 | 0.8 | |
| Ginger | 200 | 100 | 2 | |
| Green Tea Extract Powder | 70 | 60 | 1.2 | |
| Green Tea Polyphenols | 110 | 100 | 1.1 | |

Note:
1. Total anthocyanins are quantified as cyanidin-3-glucoside for all fruit samples.
2. Content of actives is calculated based on test results and percentage of active compounds. E.g., 100% of anthocyanins in elderberry, chockberry and tart cherry are actives cyanidin glycosides.
*means that COX inhibitory activities are tested from hydrolyzed and XAD column purified fruits.

In accordance with the above results, a food supplement for the treatment of inflammation preferably provides a COX-1 inhibition to a COX-2 inhibition of at least 1, and preferably greater than 1.3. As a result, the food supplement will provide a selective inhibition of COX-2.

Example 6

Specific Formulations

The present example provides formulations containing one or more fruit extracts from anthocyanin-containing plants for use as anti-inflammatory agents. Of course, these are merely exemplary formulations and those of skill in the art will understand that these formulations may be altered according to particular specifications and yet still remain equivalent to the formulations of the present invention.

TABLE 8

Anti-Inflammatory Formulation 1

| Component | 2 Unit formula | 1 unit formula | % formula |
|---|---|---|---|
| Active Ingredients: | | | |
| Elderberry Extract (min. 7% anthocyanin) | 100 mg | 50 mg | 11.277% |
| Chokeberry Extract min. 10% anthocyanin | 100 mg | 50 mg | 11.277% |
| Tart Cherry Extract | 5.00 mg | 2.50 mg | 0.564% |
| Excipient: | | | |
| Rice Powder | 675.00 mg | 337.5 mg | 76.121% |
| Magnesium Stearate | 4.50 mg | 2.25 mg | 0.507% |
| Silicone Dioxide | 2.25 mg | 1.13 mg | 0.254% |

TABLE 9

Anti-inflammatory Formulation 2

| Component | 2 Unit formula | 1 unit formula | % formula |
|---|---|---|---|
| Active Ingredients: | | | |
| Elderberry Extract (min. 13% anthocyanin) | 100 mg | 50 mg | 11.855% |
| Chokeberry Extract (min. 10% anthocyanin) | 100 mg | 50 mg | 11.855% |
| Tart Cherry Extract | 5.00 mg | 2.50 mg | 0.593% |
| Other Anti-inflammatory Herbal Extract: | 600.00 mg | 300.00 mg | 71.132 |
| Boswellia serrata extract (min. 65% boswellic acids) | | | |
| Excipient: | | | |
| Rice Powder | 1125.00 mg | 12.50 mg | 2.964% |
| Magnesium Stearate | 9.00 mg | 4.50 mg | 1.067% |
| Silicone Dioxide | 4.50 mg | 2.25 mg | 0.533% |

Table 10

Anti-inflammatory Formulation 3

| Component | 2 Unit formula | 1 unit formula | % formula |
|---|---|---|---|
| Active Ingredients: | | | |
| Elderberry Extract (min. 13% anthocyanin) | 100 mg | 50 mg | 5.905% |
| Chokeberry Extract (min. 10% anthocyanin) | 100 mg | 50 mg | 5.905% |
| Tart Cherry Extract | 5.00 mg | 2.50 mg | 0.295% |
| Other Anti-inflammatory Herbal Extract: | | | |
| Boswellia serrata extract (min. 65% boswellic acids) | 600.00 mg | 300.00 mg | 35.430% |
| Ginger Extract (min. 5% gingerols) | 500.00 mg | 125.00 mg | 29.525% |
| Excipient: | | | |
| Rice Powder | 375.00 | 93.75 | 22.143% |
| Magnesium Stearate | 9.00 mg | 2.25 mg | 0.531% |
| Silicone Dioxide | 4.50 mg | 1.13 mg | 0.266% |

TABLE 11

Pain/Inflammation relief formulation

| Component | % formula | Mg of anthocyanin provided in a single unit dosage 1 unit formula |
|---|---|---|
| Elderberry Extract (min. 7% anthocyanin) | 33% | 32 mg |
| Bilberry Extract | 3.5% | 2 mg |
| Tart Cherry Extract | 3.5% | .4 mg |
| Excipients | 60% | N/A |

Example 7

Thirty-seven men and women were selected to participate in an open-label trial to determine the pain relief capability of a berry blend dietary supplement. The dietary supplement used in this trial was comprised of elderberry, bilberry, and tart cherry, as described in Table 11. The supplement contained about 34 mg of anthocyanins total in a single tablet. The participants were randomized into One Tablet or Two Tablets groups. Subjects in the One Tablet group were instructed to take one, and subjects in the Two Tablets group were instructed to take two, Berry Blend tablets to relieve episodes of mild pain as needed. Subjects recorded their pain on a 10-cm visual analogue scale (VAS; 0=no pain, 10=worst possible pain) before as well as 30 to 45 min after taking Berry Blend. If pain relief was inadequate subjects were free to take their regular pain medication once they had recorded their "After" pain intensity on the VAS.

Figure 2:
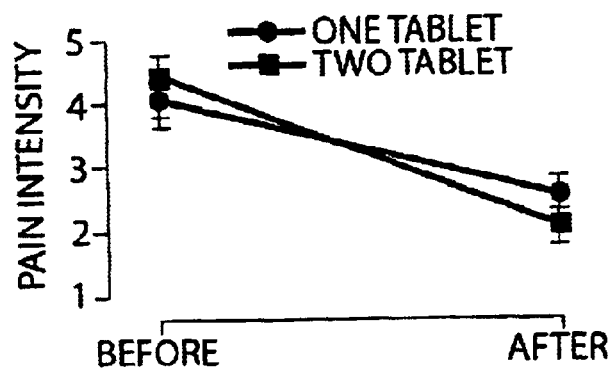
FIG. 2 is a visual analogue scale rating pain intensity before and after taking one or two tablets of a berry blend supplement in accordance with the present invention and Example 7.
Figure 3:
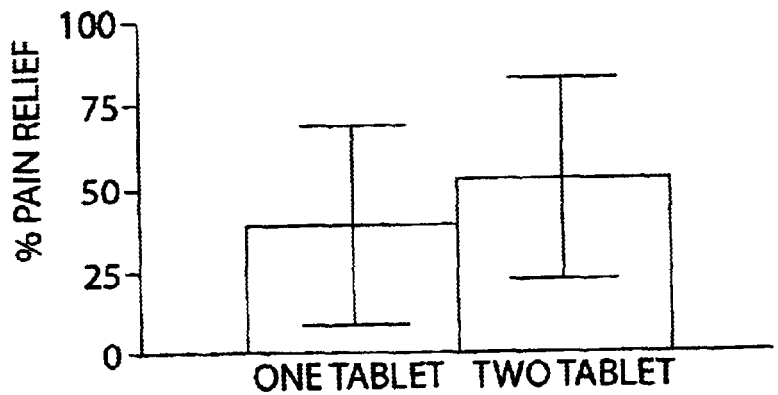
FIG. 3 shows the percentage of pain relief after taking one or two tablets of a berry blend supplement in accordance with the present invention and Example 7.

The predefined success criterion was greater pain relief in the Two Tablets than in the One Tablet group, as measured by group mean percent pain reduction in a one-tailed t-test with alpha set at 0.05. Subjects in the One and Two Tablets group had equivalent baseline VAS-rated pain [means±standard deviation for one and two tablet groups respectively: 4.11+1.38 and 4.35+1.71, t(35)=0.47, p=0.64, two-tailed]. After consumption of the test products both groups reported pain reduction (FIG. 2), with a trend towards the Two Tablets group showing greater mean percent pain reduction than the One Tablet group [One Tablet: 38.7%±30.1; Two Tablets: 52.4%±29.9, t(35)=1.52, p=0.07, one-tailed] (FIG. 3).

Figure 4:
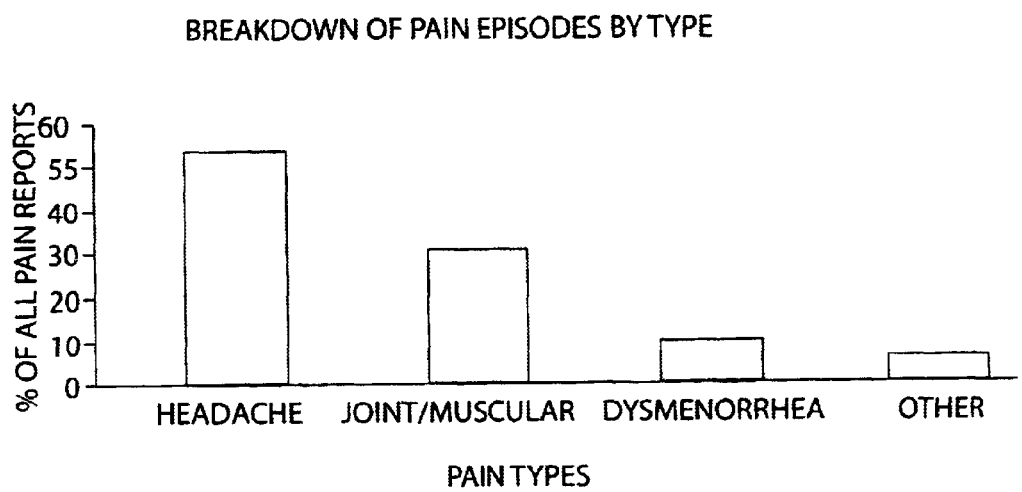
FIG. 4 shows the breakdown of pain episodes by types for the clinical trial described in Example 7.

In this trial, Headaches were the most common pain type, representing over half of all reports (FIG. 4). Next most common was joint/muscular, a combined category where no attempt was made to differentiate by diagnosis or history of disease; about one third of reports were in this category. Dysmenorrhea represented about 7–12% of pain reports and a final "other" category, for cases not captured by the preceding categories, represented about 5% of reports. There were not enough subjects in each of these categories to allow analysis of differential pain relief by pain category.

Figure 5:
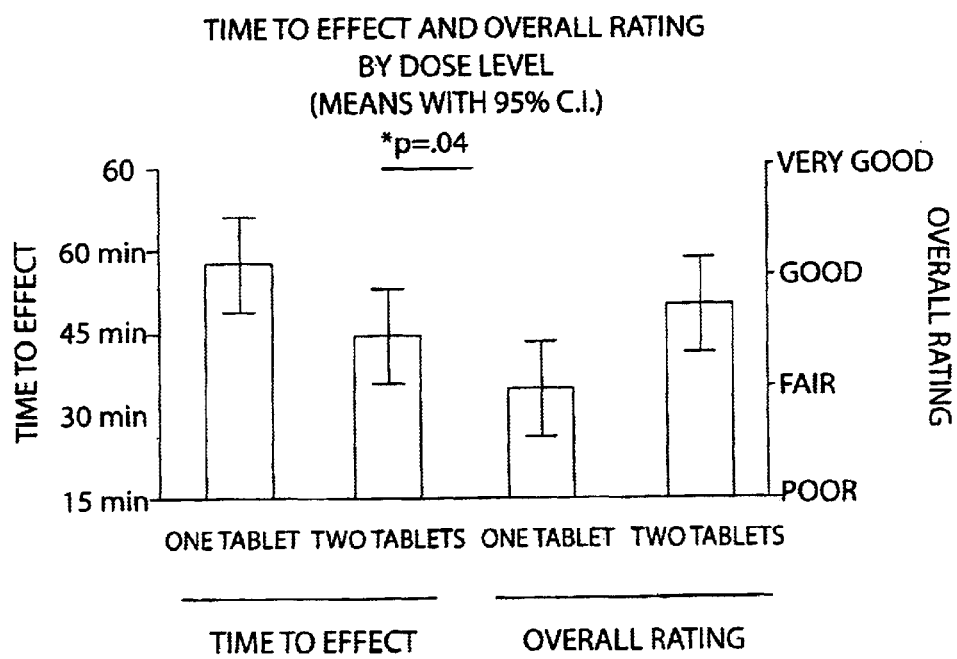
FIG. 5 shows the time to effect pain relief and the overall rating of one or two tablets of a berry blend supplement in accordance with the present invention and Example 7.

Subjects were also asked to estimate how long the product took before meaningful pain relief was felt (on a catergorical scale of 15 min to over 60 min), and to give an "approval" rating of how they thought the product worked for them (from Poor to Excellent). Two tablets took significantly less time to provide pain relief than did one tablet [about 45 min vs. about 60 min, t(35)–1.7, p=0.04, one-tailed comparison of categorical time-to-relief] (FIG. 5). The overall "approval" rating was slightly higher for the double dose than the single dose [t(35)=1.5, p=0.07, one-tailed], and for both this was somewhere between "fair" and "good."

Example 8

The same participants in the trial described in Example 7 were tested one week apart with ibuprofen 400 mg and Berry Blend two tablets followed by the same challenge, a 500-ml water-based sucrose solution. In this test, the participants drank a solution containing a measured amount of sucrose (table sugar), and a 5-h collection of their urine was assayed for sucrose concentrations. When gastric tissue is intact, sucrose is digested in the stomach and can not be found intact in the urine. When there are ulcers or minute erosions in the gastric lining which can precede ulcers, sucrose leaks through the gastric tissue before it can reach the stomach. The sucrose is then eventually excreted intact in the urine. As such, urinary sucrose concentrations serve as an index of gastric damage such as erosions in the gastric lining and gastric or intestinal ulceration.

Figure 6:
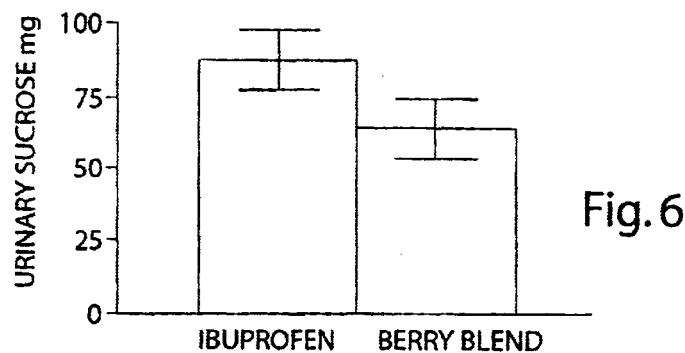
FIG. 6 shows the comparative sucrose permeability of ibuprofin and a berry blend supplement in accordance with the present invention and Example 7.

Subjects had less sucrose permeability following Berry Blend than following ibuprofen [t(5)=2.9, p=0.04, two-tailed Wilcoxon matched pairs] (FIG. 6), suggesting Berry Blend is gentler to the gastric mucosa than ibuprofen.

Example 9

Figure 7:
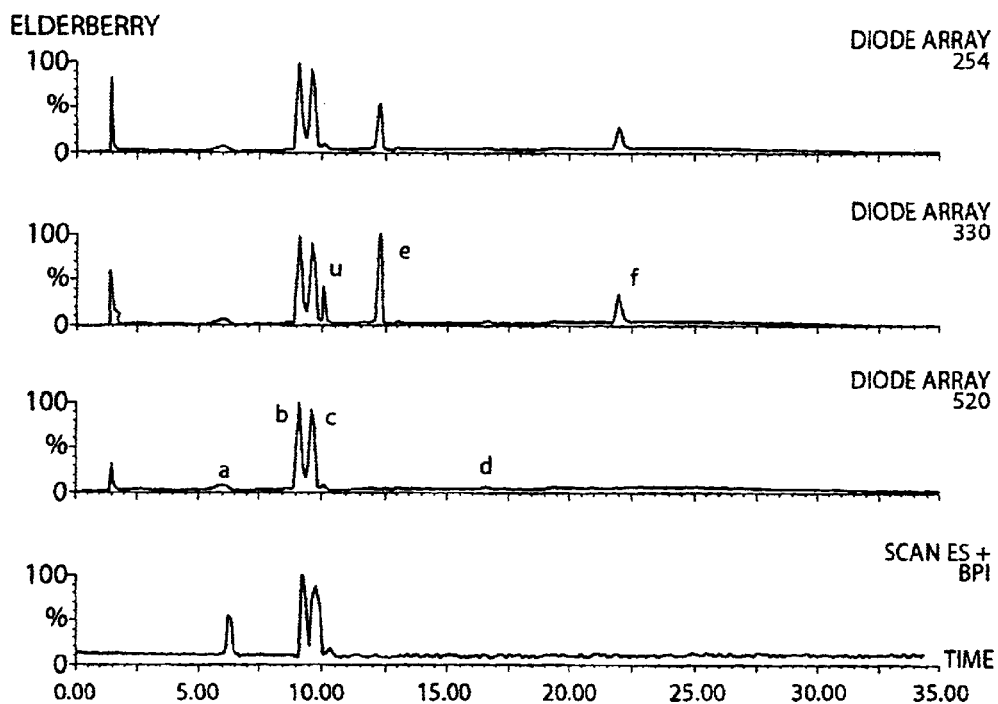
Figure 8:
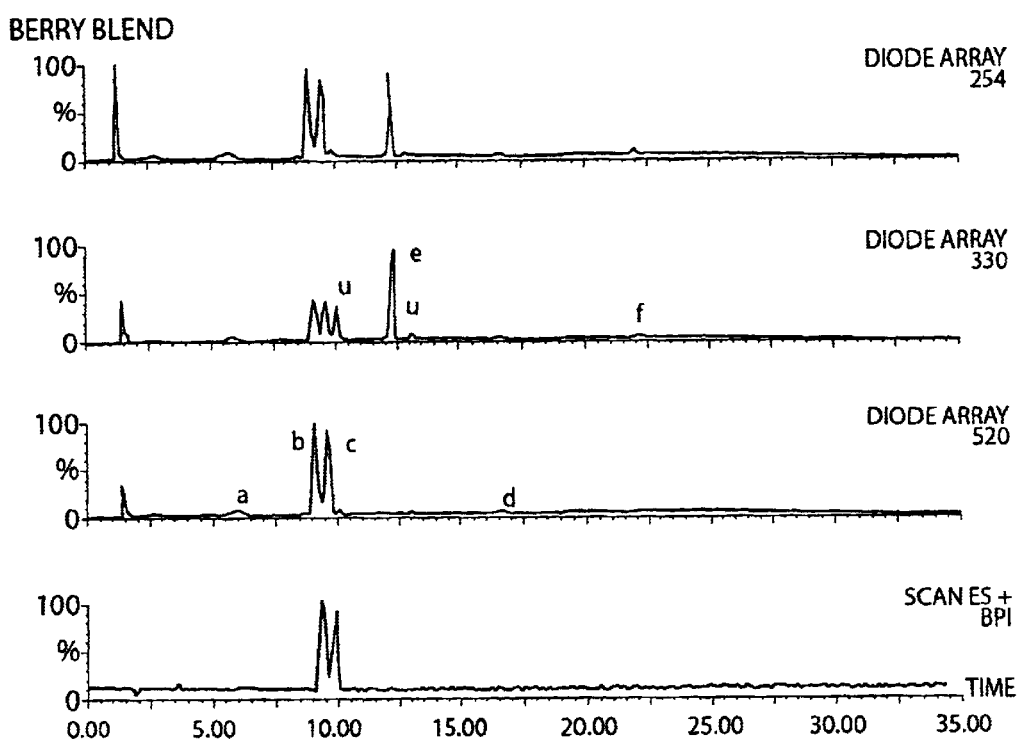

Two dietary supplements were analyzed qualitatively by LC-MS and PDA. The first supplement contained elderberry powder. The results of this analysis are shown in FIG. 7. The second supplement is a combination of elderberry, bilberry and tart cherry as described in Table 11. The results of this analysis are shown in FIG. 8. The following is a key for the compounds shown in FIGS. 7 and 8:

Compound a=Cyanidin-3-sambubioside-5-glucoside (M+=743)
Compound b=Cyanidin-3-sambubioside (M+=581)
Compound c=Cyanidin-3-glucoside (M+=449)
Compound d=Cyanidin (M+=287)
Compound e=Rutin (M+1=611)
Compound f=Quercetin (M+1=303)
Compound g=Chlorogenic acid (M+1=335)
Compounds u/A=unspecified anthocyanins
Compounds u=unidentified flavones and polyphenolic compounds All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

What is claimed is:

1. A method of alleviating or reducing pain in a mammal that comprises administering an effective amount of an anthocyanin extract extracted from an elderberry plant to a mammal that is experiencing pain, wherein the extract comprises a mixture of anthocyanins that include cyanidin-3-glucoside, cyanidin-3,5-diglucoside, cyanidin-3-sambubioside, and cyanidin-3-sambubioside-5-glucoside, whereby the mixture of the anthocyanins comprises at least about 90% of the total extract, and wherein the extract is substantially free of anthocyanidins and the extract provides greater cyclooxygenase 2 (COX-2) inhibitory activity than cyclooxygenase 1 (COX-1) inhibitory activity.

2. The method of claim 1 wherein the pain is due to a condition selected from the group consisting of arthritis, dysmenorrhea, headache, joint pain, muscular pain, osteoarthritis, and combinations thereof.

3. The method of claim 1 wherein the mammal is further administered an anthocyanin extract extracted from a tart cherry plant and a bilberry plant.

4. The method of claim 1 wherein the mammal is farther administered an anthocyanin extract extracted from a tart cherry plant.

5. The method of claim 1 wherein the mammal is further administered an anthocyanin extract extracted from a bilberry plant.

6. The method of claim 4 wherein the tart cherry plant is a variety selected from Balaton, Montanorency and mixtures thereof.

7. The method of claim 1 wherein the pain is an acute pain.

8. The method of claim 1 wherein the pain is a chronic pain.

9. The method of claim 1 wherein the extract does not produce significant erosions in the gastric lining.

10. The method of claim 1 wherein the extract does not exhibit a significant propensity to induce gastric or intestinal ulceration.

11. The method of claim 1 wherein the extract is provided in a unit dosage form and wherein each dosage provides at about 20 to 50 mg of anthocyanins.

12. The method of claim 1 wherein the extract is provided in a unit dosage form and wherein each dosage provides at least about 25 mg of anthocyanins.

13. The method of claim 1 wherein the anthocyanin extract is provided in a unit dosage form and each dosage provides about 70 mg of anthocyanins.

14. The method of claim 1 wherein the mammal is a human, the dosage form is an oral dosage form, and the extract is provided by oral ingestion.

15. The method of claim 14 wherein after oral ingestion, the extract does not produce significant erosions in gastric lining.

* * * * *